US006878364B2

(12) United States Patent
Dubovi et al.

(10) Patent No.: US 6,878,364 B2
(45) Date of Patent: Apr. 12, 2005

(54) ANIMAL MODEL FOR FLAVIVIRIDAE INFECTION

(75) Inventors: Edward J. Dubovi, Ithaca, NY (US); Bud C. Tennant, Ithaca, NY (US); James R. Jacob, Cortland, NY (US)

(73) Assignee: Cornell Research Foundation, Inc., Ithaca, NY (US)

( * ) Notice: Subject to any disclaimer, the term of this patent is extended or adjusted under 35 U.S.C. 154(b) by 272 days.

(21) Appl. No.: 10/006,524

(22) Filed: Dec. 3, 2001

(65) Prior Publication Data

US 2003/0037353 A1 Feb. 20, 2003

Related U.S. Application Data

(60) Provisional application No. 60/250,638, filed on Dec. 1, 2000.

(51) Int. Cl.[7] .............................. C11Q 1/18; C12N 5/06; A61K 49/00; C12Q 1/70
(52) U.S. Cl. ............................ 424/9.2; 435/325; 435/5; 435/32
(58) Field of Search ............................ 435/325, 5, 32; 424/9.2; 800/3, 8, 9

(56) References Cited

U.S. PATENT DOCUMENTS

| | | |
|---|---|---|
| 3,798,209 A | 3/1974 | Witkowski et al. |
| RE29,835 E | 11/1978 | Witkowski et al. |
| 5,128,458 A | 7/1992 | Montgomery et al. |
| 5,372,808 A | 12/1994 | Blatt et al. |
| 5,446,029 A | 8/1995 | Eriksson et al. |
| 5,491,135 A | 2/1996 | Blough |
| 5,610,054 A | 3/1997 | Draper |
| 5,676,942 A | 10/1997 | Testa et al. |
| 5,725,859 A | 3/1998 | Omer |
| 5,738,845 A | 4/1998 | Imakawa |
| 5,830,455 A | 11/1998 | Valtuena et al. |
| 5,837,257 A | 11/1998 | Tsai et al. |
| 5,846,964 A | 12/1998 | Ozeki et al. |
| 5,849,696 A | 12/1998 | Chretien et al. |
| 5,849,800 A | 12/1998 | Smith |
| 5,858,389 A | 1/1999 | Elsherbi |
| 5,869,253 A | 2/1999 | Draper |
| 5,891,874 A | 4/1999 | Colacino et al. |
| 5,908,621 A | 6/1999 | Glue et al. |
| 5,922,757 A | 7/1999 | Chojkier |
| 5,922,857 A | 7/1999 | Han et al. |
| 5,928,636 A | 7/1999 | Alber et al. |
| 5,942,223 A | 8/1999 | Bazer et al. |
| 5,969,109 A | 10/1999 | Bona et al. |
| 5,972,347 A | 10/1999 | Eder et al. |
| 5,980,884 A | 11/1999 | Blatt et al. |
| 5,990,276 A | 11/1999 | Zhang et al. |
| 6,001,799 A | 12/1999 | Chretien et al. |
| 6,001,990 A | 12/1999 | Wands et al. |
| 6,004,933 A | 12/1999 | Spruce et al. |
| 6,027,729 A | 2/2000 | Houghton et al. |
| 6,030,960 A | 2/2000 | Morris-Natschke et al. |
| 6,034,134 A | 3/2000 | Gold et al. |
| 6,043,077 A | 3/2000 | Barber et al. |
| 6,056,961 A | 5/2000 | Lavie et al. |

FOREIGN PATENT DOCUMENTS

WO  WO 99/29350  6/1999

OTHER PUBLICATIONS

Baker, J.A. et al. "Viral Diarrhea in Cattle" *Am. J. Vet. Res.*, (Oct. 1954) 525–531.

Bassett, S.E. et al. "Analysis of Hepatitis C Virus–Inoculated Chimpanzees Reveals Unexpected Clinical Profiles." *J. Virol.*, (Apr. 1998) 72(4):2589–2599.

Battaglia, A.M. et al., "Combination Therapy with Interferon and Ribavirin in the Treatment of Chronic Hepatitis C Infection." *Ann. Pharmacother.* (Apr. 2000) 34(4):487–494.

Berenguer, M. et al. "Hepatitis C virus in the transplant setting." *Antivir. Ther. 3.* Suppl. 3:125–136, 1998.

Cerney, A., et al. "Pathogenesis of Chronic Hepatitis C: Immunological Features of Hepatic Injury and Viral Persistence." *Hepatology* (Sep. 1999) 30(3):595–601.

Chisari, F.V., and Ferrari, C. Viral hepatitis. In: Viral Pathogenesis. Ed: Nathanson, N., et al. Lippincott–Raven Publisher, Philadelphia, 1997: 745–778.

Corapi, W.V. et al. "Characterization of a panel of monoclonal antibodies and their use in the study of the antigenic diversity of bovine viral diarrhea virus." *Am. J. Vet. Res.* (Sep. 1990) 51(9):1388–1394.

Corapi, W.V. et al. "Severe Thrombocytopenia in Young Calves Experimentally Infected with Noncyopathic Bovine Viral Diarrhea Virus." *J. Virol.*, (Sep. 1989) 63(9):3934–3943.

Cote, P.J., et al. "New Enzyme Immunoassays for the Serologic Detection of Woodchuck Hepatitis Virus Infection." *Viral Immunology* (1993) 6(2):161–169.

Cutlip, R.C. et al. "Lesions in Clinically Healthy Cattle Persistently Infected with the Virus of Bovine Viral Diarrhea—Glomerulonephritis and Encephalitis." (Dec. 1980) *Am. J. Vet. Res.*, 41(12): 1938–1941.

Davis G.L. "Current Therapy for Chronic Hepatitis C." *Gastroenterology* (2000) 118:S104–S114.

Dibisceglie, A.M., et al. "The Unmet Challenges of Hepatitis C." *Scientific American,* (Oct. 1999): 80–85.

(Continued)

*Primary Examiner*—Mary E. Mosher
(74) *Attorney, Agent, or Firm*—Sherry M. Knowles; Stephanie D. Adams; King & Spalding LLP

(57) ABSTRACT

The present invention is a woodchuck or an isolated woodchuck cell infected with bovine viral diarrhea virus. The invention can be used to identify new compounds for the treatment of flavivirus, pestivirus or hepatitis C infection using these models.

17 Claims, 17 Drawing Sheets

OTHER PUBLICATIONS

Fernelius, A.L. et al. "Bovine Viral Diarrhea Virus–Host Cell Interactions: Adaptation, Propagation, Modification, and Detection of Virus in Rabbits." (Sep. 1969) *Am. J. Vet. Res.,* 30 (9): 1541–1550.

Gerin, J.L., et al. "Hepatitis B Virus and Live Cancer: The Woodchuck as an Experimental Model of Hepadnavirus–induced Liver Cancer." *Viral Hepatitis and Hepatocellular Carcinoma.* (1990) Eds. Hollinger, F.B., et al., Williams & Wilkins Publishers, Baltimore, 1990:556–559.

Haines, D.M. et al. "Monoclonal antibody–based immunohistochemical detection of bovine viral diarrhea virus in formalin–fixed, parraffin–embedded tissues." *Vet. Path.,* (1992) 29:27–32.

Hoofnagle, J.H., et al. "Drug Therapy: The Treamtent of Chronic Viral Hepatitis." *New Engl. J. Med.,* (1997) 336(5):337–356.

Hornbuckle, W.E., et al. "Laboratory Assessment of Hepatic Injury in the Woodchuck (*Marmota Monax*)." *Lab. Anim. Sci.,* (Aug. 1985) 35:376–381.

Houe, H. "Epidemiological features and economical importance of bovine virus diarrhoea virus (BVDV) infections." *Veterinary Microbiology,* (1999) 64:89–107.

Houghton, M. "Hepatitis C Viruses." *Fields Virology,* $3^{rd}$ ed. Eds. Fields, B.H., et al. Lippencott–Raven Publishers, Philadelphia, 1996: 1035–1058.

Jacob, J.R. et al. "Characterization and Immortalization of Woodchuck Hepatocytes Isolated from Normal and Hepadnavirus–Infected Woodchucks (*Marmota monas*)." *Experimental Cell Research.* (1994) 212:42–48.

Jacob, J.R. et al. "Hepatic Expression of the Woodchuck Hepatitis Virus X–Antigen During Acute and Chronic Infection and Detection of a Woodchuck Hepatitis Virus X–Antigen Antibody Response." *Hepatology* (Dec. 1997) 26(6):1607–1615.

Jaeckel et al., "Treatment of Acute Hepatitis C with Interferon Alfa–2b." *N. England J. Med.,* (Nov. 15, 2001), 345(20):1452–1457.

Liess, B. "Bovine viral diarrhea virus." *In: Virus infections of ruminants.* B. Morein and Z. Dinter eds: Elsevier Science Ltd, 1990.

Menne, S. et al.. "T–Cell Response to Woodchuck Hepatitis Virus (WHV) Antigens during Acute Self–Limited WHV Infection and Convalescence and after Viral Challenge." *J. Virol.,* (Jul. 1998) 72(7):6083–6091.

Menne, S., et al. "Unraveling hepatitis B virus infection of mice and men (and woodchucks and ducks)." *Nature Med.,* (Oct. 1999) 5(10):1125–1126.

Meyers, G., et al. "Molecular Characterization of Pestiviruses." *Adv. In Virus Res.,* (1996) 47: 53–118.

Miller, R.H., et al. "Hepatitis C virus shares amino acid sequence similarity with pestiviruses and flaviviruses as well as members of two plant virus supergroups." *Proc. Natl. Acad. Sci. USA* (Mar. 1990) 87:2057–2061.

Negro, F. et al. "Detection of intrahepatic replication of hepatitis C virus RNA by in situ hybridization and comparison with histopathology." (Mar. 1992) *Proc. Natl. Acad. Sci. USA,* 89:2247–2251.

Ohmann, H. et al.. "Demonstration of Bovine Viral Diarrhea Virus in Peripheral Blood Mononuclear Cells of Persistently Infected, Clinically Normal Cattle." *J. Gen. Virol.* (1987) 68: 1971–1982.

Perez, J. et al. "Mutants of the Rous Sarcoma Virus Envelope Glycoprotein that Lack the Transmembrane Anchor and Cytoplasmic Domains: Analysis of Intracellular Transport and Assembly into Virions." *J. Virol.,* (Oct. 1987) 61(10):2981–2985.

Ponzetto, A. et al. "Transmission of the hepatitis B virus–associated $\delta$ agent to the eastern woodchuck." (Apr. 1984) *Proc. Natl. Acad. Sci. USA,* 81: 2208–2212.

Rice, C.M. "Flaviviridae: The Viruses and Their Replication." *Fields Virology,* $3^{rd}$ ed. eds. Fields, B.H., et al., Lippencott–Raven Publishers, Philadelphia, 1996: 931–959.

Thur, B. et al. "Immunohistochemical diagnosis of pestivirus infection associated with bovine and ovine abortion and perinatal death." (Dec. 1997) *Am. J. Vet. Res.,* 58(12): 1371–1375.

Jacob, J.R. et al. *Antiviral Therapy,* (2000) vol. 5 Suppl. 1: p. 50.

Jacob, J.R. et al. *Antiviral Therapy,* (2000) vol. 5 Suppl. 1: p. C87.

Jacob, J.R. et al. $7^{th}$ *International Meeting on Hepatitic C Virus and Related Viruses: Conference Program and Book of Abstracts* (Dec. 3–7, 2000) P095.

FIG. 3A

BVDV NY-1

- Dam 9187 (uninfected)
- 9187 pup-1
- 9187 pup 2
- 9187 pup-3

SDH (U/L) vs Time post infection (weeks)

FIG. 7

ANIMAL MODEL FOR FLAVIVIRIDAE INFECTION

This invention claims priority to U.S. provisional application No. 60/250,638 filed Dec. 1, 2000.

FIELD OF INVENTION

This invention is a woodchuck or woodchuck cell infected with a bovine viral diarrhea virus and their use as models of Flaviviridae infection.

BACKGROUND OF THE INVENTION

Infection with hepatitis C virus (HCV) has a major medical impact worldwide leading to chronic infections, cirrhosis of the liver and cancer (Di Bisceglie, A. M., and Bacon, B. R. (1999) Scientific American (Oct.): 80–85). Worldwide over 100 million people are chronically infected (Alter, M. J. (1997) Hepatology, 26(suppl. 1): 62S–65S; Hoofnagle, J. H., and DiBisceglie, A. M. (1997) New Engl. J. Med., 336: 337–356). In the U.S. almost 4 million people are chronically infected, and almost 9,000 people die annually from the disease (Chisari, F. V., and Ferrari, C. (1997) Viral hepatitis. In: Viral Pathogenesis. Ed: Nathanson, N., et al. Lippincott-Raven Publishers, Philadelphia, 1997: 745–778). The chimpanzee (*Pan troglodites*) is the only animal model with which to study the pathogenesis of hepatitis C virus (HCV) infection of humans (Houghton, M. Hepatitis C Viruses. In: Fields Virology, third edition. Eds; Fields, B. H., Knipe, D. M., Howley, P. M., et al. Lippencott-Raven Publishers, Philadelphia, 1996: 1035–1058).

HCV is a member of the viral Family Flaviviridae which are viruses that contain a positive sense, single-stranded RNA genome within an enveloped core (Miller, R. H., and Purcell, R. H. (1990) Proc. Natl. Acad. Sci. USA, 87: 2057–2061). Related members of this viral family which use similar genomic organization and replication strategies are the flaviviruses, pestiviruses, and hepatitis C viruses (Rice, C. M. Flaviviridae: The Viruses and Their replication. In: Fields Virology, third edition. Fields, B. H., Knipe, D. M., and Howley, P. M., et al, eds. Lippencott-Raven Publishers, Philadelphia, 1996: 931–959). A related pestivirus is bovine viral diarrhea virus (BVDV) which is infectious to cattle and can lead to persistent infections. Pestivirus diseases are widespread and still of economic importance to the livestock industry (Houe, H. (1999) Veterinary Microbiology, 64: 89–107).

Bovine viral diarrhea virus (BVDV), as first described by Baker et al, was transmitted to and serially passaged in rabbits (Baker, J. A. et al. (1954) Am. J. Vet. Res., Oct.1954: 525–531). Further investigation led to the adaptation of BVDV to rabbits and selecting a 'biotype' which was less cytopathic (Fernelius, A. L. et al. (1969) Am. J. Vet. Res., 30 (9): 1541–1550). These early studies demonstrated transmission of a viral pathogen, considered restricted to ruminant species, to a more convenient laboratory animal model.

The woodchuck infected with the woodchuck hepatitis virus (WHV) is an art recognized and accepted model for investigation of the pathogenesis of hepatitis B virus (HBV) infections of humans (Menna, S., and Tennant, B. C. (1999) Nature Med., 5(10): 1125–1126). This animal model has been instrumental in the development of antiviral treatments for chronic hepadnaviral (WHV, HBV) infections (Korba, B. E., et al. Woodchuck Virus Infection as a Model for the Development of Antiviral Therapies Against HBV. In: Viral Hepatitis and Liver Disease. Eds: Hollinger, F. B., Lemon, S. M., and Margolis, H. S., Williams and Wilkens, Baltimore, 1991: 556–559). Additionally, the human delta hepatitis virus has been adapted to infection of woodchucks as an alternative model to the chimpanzee (Taylor, J. et al. (1987) J. Virol., 61: 2981–2985; Ponzetto, A. et al. (1984) Proc. Natl. Acad. Sci. USA, 81: 2208–2212).

A significant focus of current antiviral research is directed to the development of improved methods of treatment of chronic HCV infections in humans (Di Besceglie, A. M. and Bacon, B. R., Scientific American, Oct.: 80–85, (1999). Discovery of new treatments for the treatment of HCV has been hindered by the lack of suitable animal models. Currently, the only antiviral drugs available toward the treatment of chronic HCV infection in humans are alpha-interferon and ribavirin (Hoofnagle, J. H., and DiBisceglie, A. M. (1997) New Engl. J. Med., 336: 337–356).

BVDV is often used as a model for the development of HCV surrogate molecular target assays, because of the difficulties of growing HCV in vitro. BVDV and HCV have a high degree of genetic homology, common replication strategies and it is believed the same sub-cellular location for viral envelopment (Collet, M. S. (1992) Comp. Immun. Micro. Infect. Dis. 15, 145–155).

The nucleotide sequence of the RNA genome of the human hepatitis C virus (HCV) has been determined from overlapping cDNA clones. The sequence (9379 nucleotides) has a single large open reading frame that could encode a viral polyprotein precursor of 3011 amino acids. While there is little overall amino acid and nucleotide sequence homology with other viruses, the 5' HCV nucleotide sequence upstream of this large open reading frame has substantial similarity to the 5'-termini of pestiviral genomes, in particular BVDV. A portion of the 5'-UTR (a 332–341 nucleotide region) contains a sequence with a 47% sequence homology to bovine viral diarrhoea virus (BVDV).

The polyprotein from the open reading frame of HCV also has significant sequence similarity to the NTP-binding helicases (approximately between amino acids 1230 and 1500) encoded by animal pestiviruses, and it contains sequence motifs widely conserved among viral-encoded RNA-dependent RNA polymerase (between amino acids 2703–2739, containing six highly conserved residues) and trypsin-like proteases. A basic, presumed nucleocapsid domain is located at the N terminus upstream of a region containing numerous potential N-linked glycosylation sites. These HCV domains are located in the same relative position as observed in the pestiviruses and flaviviruses and the hydrophobic profiles of all three viral polyproteins are similar. (Choo, et al. "Genetic organization and diversity of the hepatitis C virus" 1991, Proc. Natl. Acad. Sci. 88, 2451–2455).

In addition, BVDV and HCV both have an NS4A cofactor requirement for the NS3 serine protease; and BVDV exhibits polyprotein cleavages similar to that seen in HCV, which occur in the nonstructural region (NS5 A/B).

Treatment of HCV Infection with Ribavirin

Ribavirin (1-β-D-ribofuranosyl-1-1,2,4-triazole-3-carboxamide) is a synthetic, non-interferon-inducing, broad spectrum antiviral nucleoside analog sold under the trade name Virazole™ (The Merck Index, 11th edition, Editor: Budavari, S., Merck & Co., Inc., Rahway, N.J., p1304, 1989). U.S. Pat. Nos. 3,798,209 and RE29,835 disclose and claim ribavirin.

Ribavirin is structurally similar to guanosine, and has in vitro activity against several DNA and RNA viruses including Flaviviridae (Davis. Gastroenterology 118:S104–S114, 2000). Ribavirin reduces serum amino transferase levels to normal in 40% of patients, but it does not lower serum levels of HCV-RNA (Davis. Gastroenterology 118:S104–S114, 2000). Thus, ribavirin alone is not effective in reducing viral RNA levels. Additionally, ribavirin has significant toxicity and is known to induce anemia.

Treatment of HCV Infection with Interferon

Interferons (IFNs) are compounds which have been commercially available for the treatment of chronic hepatitis for nearly a decade. IFNs are glycoproteins produced by immune cells in response to viral infection. IFNs inhibit viral replication of many viruses, including HCV, and when used as the sole treatment for hepatitis C infection, IFN suppresses serum HCV-RNA to undetectable levels. Additionally, IFN normalizes serum amino transferase levels. Unfortunately, the effects of IFN are temporary and a sustained response occurs in only 8%–9% of patients chronically infected with HCV (Davis. Gastroenterology 118:S104–S114, 2000). A recent study, however, has indicated that early and prompt treatment with an interferon analogue, interferon alpha-2b of patients acutely infected with HCV can prevent chronic infection in 98% of the patients (Jaeckel et al, N.Engl. J. Med., Nov. 15, 2001, 345).

A number of patents are directed to the use of interferons to treat HCV infection. For example, U.S. Pat. No. 5,980,884 to Blatt et al. discloses methods for treatment of patients afflicted with HCV using consensus interferons.

U.S. Pat. No. 5,942,223 to Bazer et al. discloses an anti-HCV therapy using ovine or bovine interferon-tau.

U.S. Pat. No. 5,928,636 to Alber et al. discloses the combination therapy of interleukin-12 and interferon alpha for the treatment of infectious diseases including HCV.

U.S. Pat. No. 5,908,621 to Glue et al. discloses the use of polyethylene glycol modified interferon for the treatment of HCV.

U.S. Pat. No. 5,849,696 to Chretien et al. discloses the use of thymosins, alone or in combination with interferon, for treating HCV.

U.S. Pat. No. 5,830,455 to Valtuena et al. discloses a combination HCV therapy employing interferon and a free radical scavenger.

U.S. Pat. No. 5,738,845 to Imakawa discloses the use of human interferon tau proteins for treating HCV. Other interferon-based treatments for HCV are disclosed in U.S. Pat. No. 5,676,942 to Testa et al., and U.S. Pat. No. 5,372,808 to Blatt et al.

Combination of Interferon and Ribavirin

The combination of IFN and ribavirin for the treatment of HCV infection has been reported to be effective in the treatment of IFN naïve patients. (Battaglia, A. M. et al., Ann. Pharmacother. 34:487–494, 2000). Results are promising for this combination treatment both before hepatitis develops or when histological disease is present (Berenguer, M. et al. Antivir. Ther. 3(Suppl. 3):125–136, 1998). Side effects of combination therapy include hemolysis, flulike symptoms, anemia, and fatigue. (Davis. Gastroenterology 118:S104–S114, 2000).

Additional Treatments for HCV Infections

U.S. Pat. No. 5,891,874 discloses a series of benzimidazole compounds and a method for inhibiting Flaviviridae including hepatitis C and bovine diarrheal virus using such compounds.

U.S. Pat. No. 6,056,961 discloses extracts of the plant *Hypericum perforatum* and pharmaceutical compositions thereof for the treatment of HCV infection. Other U.S. patents disclosing plant extracts for the treatment of HCV infection include: U.S. Pat. No. 5,837,257 to Tsai et al., U.S. Pat. No. 5,725,859 to Omer et al.

U.S. Pat. No. 6,001,799 discloses a method of treating hepatitis C in non-responders to interferon comprising administering at least one thymosin.

U.S. Pat. No. 5,922,757 discloses methods for the treatment of hepatitis C involving the administration of vitamin E and other compounds with antioxidant properties.

Several patents disclose protease inhibitors for the treatment of HCV. For example, U.S. Pat. No. 6,004,933 to Spruce et al. discloses a class of cysteine protease inhibitors for inhibiting HCV.

U.S. Pat. No. 5,990,276 to Zhang et al. discloses synthetic inhibitors of hepatitis C virus NS3 protease. The inhibitor is a subsequence of a substrate of the NS3 protease or a substrate of the NS4A cofactor.

U.S. Pat. No. 5,972,347 to Eder et al. and U.S. Pat. No. 5,969,109 to Bona et al. disclose a vaccine for treating HCV.

U.S. Pat. No. 6,034,134 to Gold et al. discloses certain NMDA receptor agonists having immunodulatory, antimalarial, anti-Boma virus, and anti-HCV activities. The disclosed NMDA receptor agonists belong to a family of 1-amino-alkylcyclohexanes.

U.S. Pat. No. 6,030,960 to Morris-Natschke et al. discloses the use of certain alkyl lipids to inhibit the production of hepatitis-induced antigens, including those produced by the HCV virus.

U.S. Pat. No. 5,858,389 to Elsherbi et al. discloses the use of squalene for treating hepatitis C.

U.S. Pat. No. 5,849,800 to Smith et al. discloses the use of amantadine for treatment of Hepatitis C.

U.S. Pat. No. 5,846,964 to Ozeki et al. discloses the use of bile acids for treating HCV.

U.S. Pat. No. 5,491,135 to Blough et al. discloses the use of N-(phosphonoacetyl)-L-aspartic acid to treat flaviviruses such as HCV.

U.S. Pat. No. 5,922,857 to Han et al. disclose nucleic acids corresponding to the sequence of the pestivirus homology box IV area for controlling the translation of HCV.

The use of ribozymes to treat HCV is disclosed in U.S. Pat. No. 6,043,077 to Barber et al., and U.S. Pat. Nos. 5,869,253 and 5,610,054 to Draper et al.

PCT application WO 99/29350 discloses compositions and methods of treatment for hepatitis C infection comprising the administration of antisense oligonucleotides which are complementary and hybridizable to HCV-RNA.

U.S. Pat. No. 6,001,990 discloses antisense oligonucleotides and methods of using these antisense oligonucleotides for inhibiting HCV-RNA translation.

U.S. Pat. No. 6,027,729 discloses and claims polypeptides encoded by the HCV genome.

U.S. Pat. No. 5,128,458 discloses β-D-2',3'-dideoxy-4'-thioribonucleosides as antiviral agents. U.S. Pat. No. 5,446,029 discloses that 2',3'-dideoxy-3'-fluoronucleosides have anti-hepatitis activity.

Because of the serious effect of HCV infection on a host and the widespread infection of HCV, there exists a critical need for new animal and cellular models to study the pathogenesis of Flaviviridae infections, including flavivirus, pestivirus and hepacivirus infections, particularly HCV. Moreover, there is a strong need for new compounds and methods of treating Flavivirus infections including HCV.

SUMMARY OF INVENTION

It has been discovered that the woodchuck can be infected with bovine viral diarrhea virus (BVDV). BVDV is closely related to hepatitis C virus and other members of the Flaviviridae family, including flaviviruses, pestiviruses and hepaciviruses, particularly HCV. Thus, the present invention is directed to a woodchuck infected with BVDV as a novel animal model for the pathogenesis of Flaviviridae infections, in particular hepatitis C infection. In another aspect, the invention comprises a woodchuck cell infected with BVDV.

The animal model of the present invention can provide new methods for determining the activity of compounds for treating flavivirus, pestivirus or hepatitis C infections. In one aspect of the invention, a method for determining the activity of a compound for the treatment of a flavivirus, pestivirus or hepacivirus infections, and in particular hepatitis C infections, can include: administering a test compound to a woodchuck infected with BVDV, determining the effect of the test compound on BVDV infection in the woodchuck; and selecting the compound wherein the BVDV infection of the woodchuck is reduced.

In another aspect of the invention, isolated cells from a woodchuck can be infected with BVDV. The infected cells can be maintained in vitro. An in vitro method for determining the effectiveness of a compound for the treatment of flavivirus, pestivirus, or hepatitis C infections can include: administering a test compound to a culture of woodchuck cells infected with BVDV, determining the effect of the test compound on BVDV infection in a woodchuck cell; and selecting the compound wherein the BVDV infection of the woodchuck cell is reduced.

Thus, embodiments of the present invention include:

A). A method for identifying a compound for the treatment of Flaviviridae infection comprising:
   a) administering a test compound to a woodchuck infected with bovine viral diarrhea virus; and
   b) determining whether the test compound inhibits bovine viral diarrhea virus in the woodchuck.

B). A method for identifying a compound for the treatment of a Flaviviridae infection comprising:
   a) administering a test compound to a first woodchuck infected with bovine viral diarrhea virus;
   b) administering a control compound to a second woodchuck infected with bovine viral diarrhea virus;
   c) selecting the test compound that inhibits bovine viral diarrhea virus in the first woodchuck more than the control inhibits the virus in the second woodchuck.

C). A method for identifying a compound for the treatment of a Flaviviridae infection comprising:
   a) administering a test compound to a first woodchuck infected with bovine viral diarrhea virus;
   b) infecting a second woodchuck with bovine viral diarrhea virus;
   c) selecting the test compound that decreases the load of bovine viral diarrhea virus in the first woodchuck over the viral load in the second woodchuck.

D). A method for identifying a compound for the treatment of a Flaviviridae infection comprising:
   a) administering a test compound to a woodchuck cell infected with bovine viral diarrhea virus; and
   b) determining whether the test compound inhibits the bovine viral diarrhea virus in the woodchuck cell.

E). A method for identifying a compound for the treatment of a Flaviviridae infection comprising:
   a) administering a test compound to a first woodchuck cell infected with bovine viral diarrhea virus;
   b) administering a control compound to a second woodchuck cell infected with bovine viral diarrhea virus; and
   c) determining whether the test compound inhibits bovine viral diarrhea virus in the first woodchuck cell more than the control compound inhibits bovine viral diarrhea virus in the second woodchuck cell.

BRIEF DESCRIPTION OF THE DRAWINGS

FIG. 1 is a set of line graphs showing the immune response in neonate woodchucks after inoculation with BVDV. Three one day old neonates from dam wc9187 were inoculated with ncpBVDV isolate NY-1.

FIG. 3A illustrates the liver enzyme activity in neonate woodchucks after inoculation with BVDV. One day old neonates from dam wc9187 inoculated with ncpBVDV isolate NY-1 (pup 1, 2, and 3) and uninfected controls (wc9203 pup 1, 2, 3.

FIG. 7 illustrates the infectious cpBVDV secreted into the culture supernatant of woodchuck hepatocytes after inoculation with cpBVDV. Woodchuck primary hepatocytes and hepatic WCH-8 cells were cultured and inoculated with the cytopathogenic NADL isolate of BVDV (cpBVDV). Titers of infectious cpBVDV in the culture supernatants collected at 2 day intervals post infection (p.i.) of woodchuck cells were determined in highly permissive bovine NCL cells. BVDV titers were expressed as the reciprocal of the last dilution positive for virus. Titration of virus from cpBVDV-infected WCH-8 cells ended after day 18 p.i. due to complete viral-induced cell killing (-Δ-). Infectious cpBVDV was produced from primary hepatocyte cultures for over 2 months p.i. (-●-).

DETAILED DESCRIPTION OF THE INVENTION

Figure 1A:
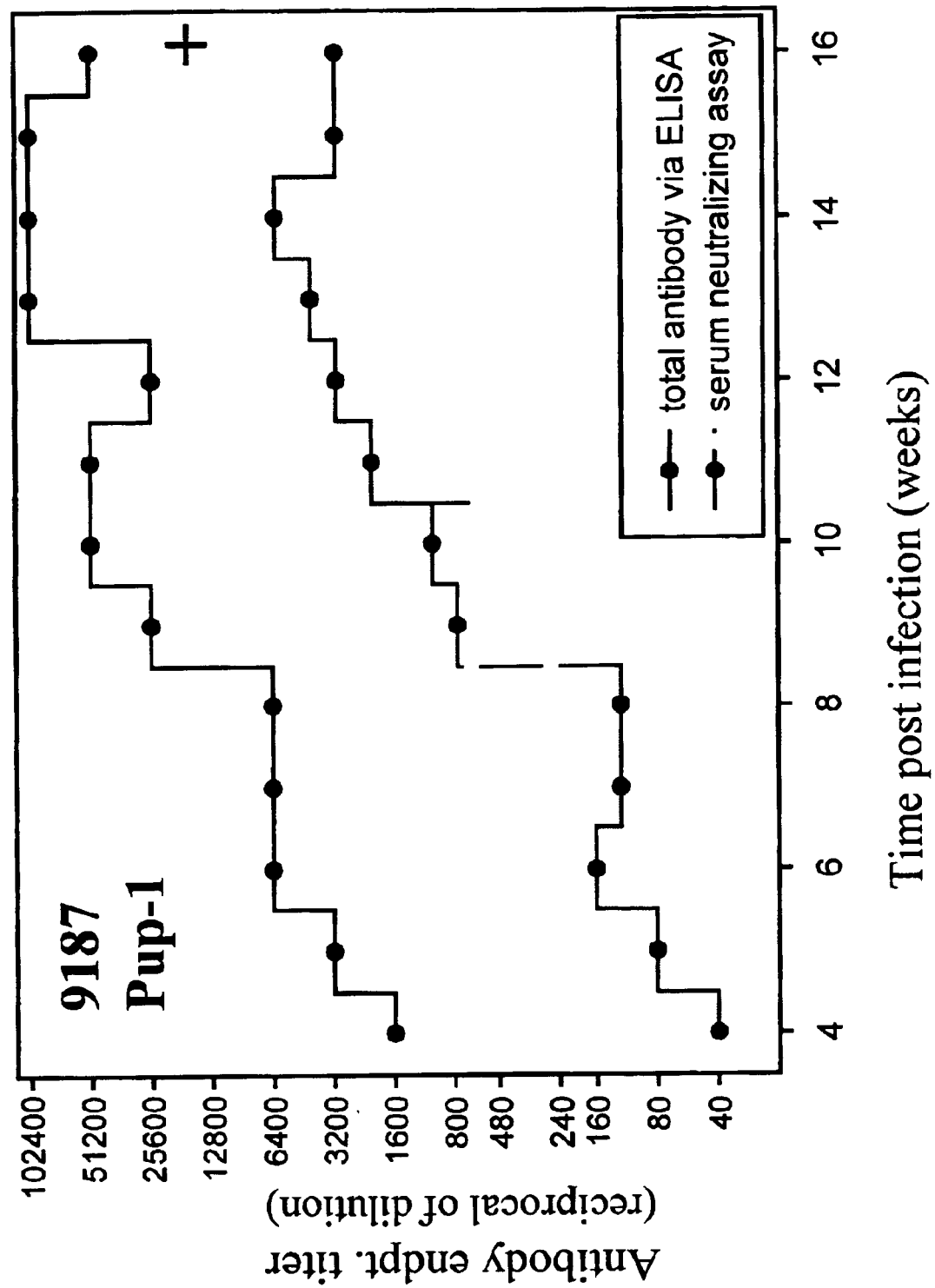
FIG. 1A shows the results from pup-1.

The present invention is founded on the surprising discovery that woodchucks, Marmota monax, can be infected with bovine viral diarrhea virus (BVDV). Woodchucks are not a natural host of BVDV. Thus, in one embodiment, the present invention is a woodchuck infected with BVDV. Woodchucks can be infected with BVDV by injecting isolated BVDV into neonate liver. In one embodiment, non-cytopathogenic isolates of BVDV are used to inoculate neonate woodchucks. BVDV infection of woodchucks can be confirmed and monitored by known methods. Such methods include but are not limited to assaying liver enzyme activity including alanine aminotransferase, aspartate aminotransferase, and sorbitol dehydrogenase; immunologic analysis; blood serum analysis; other surrogate markers; and blood counts to determine which cell differentials indicative of viral infection. In another embodiment, one can serially passage the BVDV virus in woodchucks or cell cultures thereof, to produce an inoculating virus to monitor, or test drugs.

In another embodiment of the present invention, an isolated woodchuck cell is infected with either a non-cytopathogenic or cytopathogenic isolate of BVDV. The infected woodchuck cell can be maintained in culture using cell culture techniques known in the art. For example, infected woodchuck cells can be maintained in a growth medium supplemented with a pH buffer and nutrients such as fetal calf serum or horse serum. Serum can be supplemented in any amount, for example from about 1% to 20%. Growth factors, cytokines, antibiotics, fungicides and the like can also be added to the culture medium. Additionally, BVDV infected woodchuck cells can be cultured in serum-free culture media. Culture media is available commercially. Serial passage of the BVDV virus in woodchucks or cell cultures can be used as inoculating virus to monitor or test drugs.

In another embodiment, a method for identifying compounds for the treatment of flavivirus, pestivirus or hepatitis C infection is provided that includes:

a) administering a test compound to a woodchuck infected with bovine viral diarrhea virus;
b) determining whether the test compound inhibits bovine viral diarrhea virus in the woodchuck; and
c) selecting a test compound that inhibits bovine viral diarrhea virus in the woodchuck. In one embodiment, the woodchuck is infected with a noncytopathogenic isolate of BVDV, for example, the NY1 isolate of BVDV.

In still another embodiment, a method of identifying compounds for the treatment of flavivirus, pestivirus, or hepatitis C infection is provided that includes:

a) administering a test compound to a woodchuck infected with bovine viral diarrhea virus;
b) determining whether the test compound inhibits bovine viral diarrhea virus in the woodchuck;
c) comparing the results of step (b) with results from a woodchuck infected with bovine viral diarrhea virus administered a control compound; and
d) selecting the test compound that inhibits bovine viral diarrhea virus in the woodchuck administered the test compound compared to the control compound in step (c).

In still another embodiment, a method for identifying compounds for the treatment of flavivirus, pestivirus, or hepatitis C infection is provided that includes:

a) administering a test compound to a woodchuck infected with bovine viral diarrhea virus;
b) comparing the infection in the woodchuck from step (a) to the infection in a woodchuck not administered a test compound; and
c) selecting the test compound that inhibits bovine viral diarrhea virus in the woodchuck of step (a) compared to a woodchuck in step (b).

Because hepatitis C is in the same family as BVDV, BVDV infection is a reasonable predictor of hepatitis C infection and other Flaviviridae infections. Thus, results of compounds inhibiting BVDV are generally predictive of results of the same compounds for inhibiting hepatitis C.

In one embodiment, the inhibition of bovine viral diarrhea virus can be determined by monitoring the activity of liver enzymes or levels of BVDV proteins in serum. Enzymes to be monitored include but are not limited to alanine aminotransferase, aspartate aminotransferase, and sorbitol dehydrogenase. Inhibition of BVDV can also be evaluated using immunologic analysis, blood serum analysis, other surrogate markers and blood counts to determine which cell differentials indicative of viral infection. In one embodiment, inhibition of BVDV can be determined by assessing the level of bovine viral diarrhea virus antigens present in serum.

In still another embodiment, a method for identifying compounds for the treatment of flavivirus, pestivirus, or hepatitis C infection is provided including:

a) administering a test compound to a woodchuck cell infected with bovine viral diarrhea virus;
b) determining whether the test compound inhibits bovine viral diarrhea virus in the woodchuck cell;
c) selecting the test compound that inhibits bovine viral diarrhea virus in the woodchuck cell.

BVDV infected woodchuck cells can be maintained using art known methods of cell culture as indicated above. The in vitro method of identifying compounds useful for the treatment of Flaviviridae infection can be automated. The inhibition of bovine viral diarrhea virus can be determined by monitoring BVDV proteins secreted in culture or expressed on infected cells. Inhibition of BVDV can also be determined using immunologic analysis, polymerase chain reaction, Northern Blot analysis, and other methods of virus detection known in the art.

In still another embodiment, a method for identifying compounds for the treatment of flavivirus, pestivirus, or hepatitis C infection is provided including:

a) administering a test compound to an isolated woodchuck cell infected with bovine viral diarrhea virus;
b) comparing the inhibition of the virus in the cell of step (a) to the viral growth in an isolated woodchuck cell infected with bovine viral diarrhea virus administered a control compound;
c) selecting the test compound that inhibits bovine viral diarrhea virus in the woodchuck cell administered the test compound compared to the woodchuck cell administered the control compound in step (b).

In still another embodiment, a method for identifying compounds for the treatment of flavivirus, pestivirus, or hepatitis C infection is provided including:

a) administering a test compound to an isolated woodchuck cell infected with bovine viral diarrhea virus;
b) comparing the viral growth in the cell of step (a) to the viral growth in a woodchuck cell infected with bovine viral diarrhea virus not administered a test compound;
c) selecting the test compound that inhibits bovine viral diarrhea virus in the woodchuck cell administered the test compound compared to the woodchuck cell infected with bovine viral diarrhea virus not administered a test compound in step (b).

Alternatively, the methods of the present invention can be used to assess the efficacy of certain test compounds in combination or alternation with other test compounds in the inhibition of a Flaviviridae infection, and in particular a BVDV or HCV infection, optionally in comparison to a positive or negative control, as discussed herein.

In another embodiment, the methods of the present invention can be used to assess the efficacy of certain test compounds in combination or alternation with other test compounds for the prophylaxis of a Flaviviridae infection, and in particular a BVDV or HCV infection, optionally in comparison to a positive or negative control, by administering the test compound, and optionally the positive or negative control prior to the infection of the woodchuck or isolated woodchuck cell with BVDV.

The term "isolated" as used herein refers to an ex vivo woodchuck cell.

In general the term "control compound" as used herein refers to a negative control, such as a compound that does not significantly inhibit or promote viral growth. In an alternative embodiment of the invention, the test compound can be compared to a positive control with confirmed ability to inhibit viral growth, such as a compound that has been confirmed to inhibit a Flaviviridae infection, such as BVDV or HCV, including but not limited to interferon.

The methods to determine the activity of compounds for the treatment of flavivirus, pestivirus or hepatitis C virus of the present invention can be used to screen any compound. Nonlimiting examples of compounds that can be screened by the methods of the present invention include: small organic molecules, nucleosides, nucleotides, nucleoside analogs, nucleotide analogs, oligonucleotides, antisense oligonucleotides, stabilized oligonucleotides including oligonucleotides containing a phosphorothioate or phosphoroamidate backbone or similar modified backbone, peptide mimetics, peptide nucleic acids, protease inhibitors, polymerase inhibitors, plant extracts, peptides, polysaccharides, glycoproteins, and the like.

Modes of administration of the compounds in the animal model can be parenteral, intravenous, intradermal, intraarticular, intra-synovial, intrathecal, intra-arterial, intracardiac, intramuscular, subcutaneous, intraorbital, intracapsular, intraspinal, intrasternal, topical, transdermal patch, via rectal, vaginal or urethral suppository, peritoneal, percutaneous, nasal spray, surgical implant, internal surgical paint, infusion pump, or via catheter. In one embodiment, the agent and carrier are administered in a slow release formulation such as an implant, bolus, microparticle, microsphere, nanoparticle or nanosphere. The preferred mode of administering is intravenous. For standard information on pharmaceutical formulations, see Ansel, et al., Pharmaceutical Dosage Forms and Drug Delivery Systems, Sixth Edition, Williams & Wilkins (1995).

The compounds screened for activity against flavivirus, pestivirus or hepatitis C can, for example, be administered intravenously or intraperitoneally by infusion or injection. Solutions of the substance can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The features and advantages of the present invention will be more clearly understood by reference to the following examples, which are not to be construed as limiting the invention.

EXAMPLES

Methods and Materials (Examples 1–5)

The data described in the following examples 1–5 was obtained using the following Methods and Materials.

Animals: Woodchucks were born and raised in the woodchuck breeding colony at Cornell University, Ithaca, N.Y. Animals were tested for antibodies to BVDV by a serum neutralization assay (Corpai, W. V. et al. (1990) Am. J. Vet. Res. 51: 1388–1394). In studies examining the infection of neonates, woodchucks born to dams negative for antibodies to BVDV were used. Newborn animals were split into groups of three for inoculation with BVDV or as a group of uninfected controls.

Sedation and sample collection: Adult woodchucks were anesthetized with ketamine (50 mg/kg) and xylazine (5 mg/kg) to allow pre-inoculation blood samples to be drawn for serologic evaluation of antibodies toward BVDV. Neonate woodchucks were restrained manually 4 to 8 weeks of age, and anesthetized 9 to 16 weeks of age during the time of injection and blood collection. Post-inoculation blood samples were taken from neonate animals via femoral vein weeks 4 through 16 of this protocol. The uninfected control group was bled in similar fashion on an identical time schedule. Animals were euthanized for tissue collection by lethal injection of ketamine/xylazine upon completion of this protocol.

BVDV Infection: Three neonate woodchucks were inoculated with the noncytopathogenic, NY1 isolate of BVDV (ncpBVDV). The inoculum was derived from bovine tissue culture with an end-point titer approaching $2 \times 10^7$ BVDV $TCID_{50}$/mL. An inoculum containing $2 \times 10^6$ BVDV $TCID_{50}$ (0.1 mL) was injected percutaneously into the parenchyma of the neonate liver, visualized just below the costal arch using a tuberculin syringe, one day after birth.

Immunologic Analysis: The immunoprecipitation assay was a modification of a procedure previously described (Jacob, J. R. et al. (1997) Hepatology, 26: 1607–1615). Briefly, bovine uterine cells labeled with [$^{35}$S]met-cys were extracted after infection with the cytopathogenic, NADL isolate of BVDV (cpBVDV) and woodchuck serum was used to precipitate viral antigens. The cellular proliferation assay was a modification of a procedure previously described (Menne, S. et al. (1998) J. Virol., 72(7): 6083–6091). Briefly, peripheral mononuclear blood cells (PBMC) were isolated from woodchuck whole blood and assayed for proliferation in response to antigenic stimulation using extracts of cpBVDV-infected cells and BVDV-containing tissue culture supernatants. An ELISA to detect total antibody to BVDV antigens was a modification of procedures previously described (Cote, P. J., Roneker et al. (1993) Viral Immunology, 6:161–169). Briefly, the cpBVDV-infected cell extract described above was used for capture of antibodies present in woodchuck serum. The development of serum neutralizing antibodies toward BVDV was monitored by viral serum neutralization assays (Corpai, W. V. et al. (1990) Am. J. Vet. Res. 51: 1388–1394).

A viremic phase was monitored by the recovery of infectious BVDV from woodchuck PBMC, assayed in bovine uterine cell lines by direct immunofluorescence (Corapi, W. V. et al. (1989) J. Virol., 63:3934–3943). Detection of infectious BVDV in woodchuck tissues collected at necropsy was analyzed by similar methods. Blood samples were collected and submitted for serum biochemistry profiles monitoring alanine aminotransferase (ALT), aspartate aminotransferase (AST), and sorbital dehydrogenase (SDH), as well as blood counts to determine white cell differentials indicative of viral infection (Hornbuckle, W. E. et al. (1985) Laboratory assessment of hepatic injury in the woodchuck (*Marmota monax*). Lab. Anim. Sci., 35: 376–381).

Histology: At the completion of these experimental protocols samples of the liver, kidney, spleen, lymph nodes, gonads, intestine, and pancreas were collected during necropsy and snap frozen in liquid $N_2$ or fixed in formalin. Thin sections of paraffin embedded samples were stained with hemotoxylin & eosin or stained by immunohistochemical procedures for the detection of BVDV specific antigens (Haines, D. M. et al. (1992) Monoclonal antibody-based immunohistochemical detection of bovine viral diarrhea virus in formalin-fixed, paraffin-embedded tissues. Vet. Path., 29:27–32) and evaluated by a pathologist.

Example 1

Serologic Response of Neonate Woodchucks Infected with BVDV

Figure 1B:
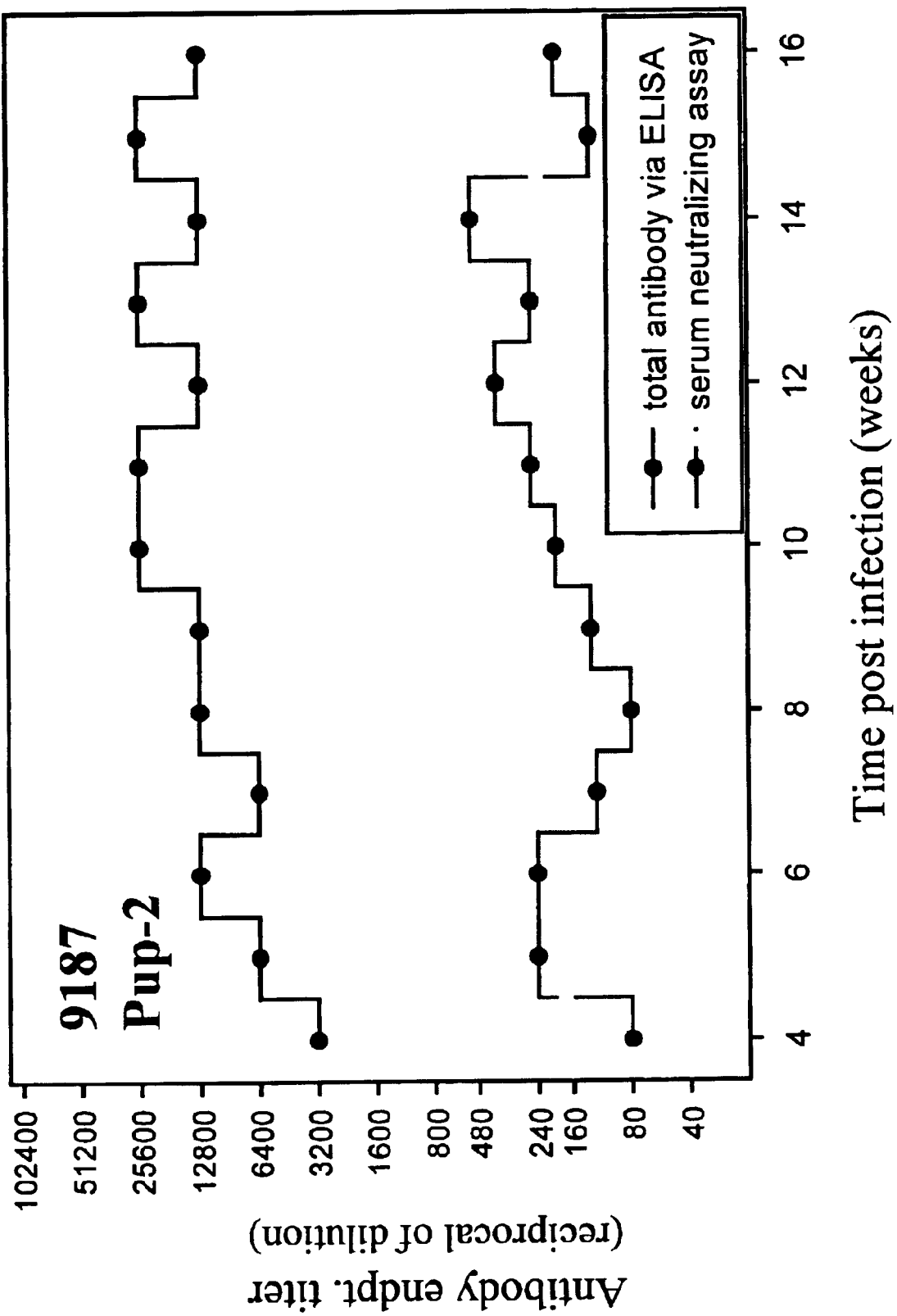
FIG. 1B shows the results from pup-2.

The result of the inoculation of neonate woodchucks and the development of an infection was investigated by monitoring the humoral immune response as an indication of BVDV replication. An antibody toward BVDV antigens was detected in the serum of all pups born to dam 9187, which were inoculated with ncpBVDV (FIG. 1). Serum was first assayed beginning at 4 weeks and continued to 16 weeks post-infection. The titer of total antibody toward BVDV antigens increased in pup-1, remained constant in pup-2, and tended to decrease in pup-3.

Figure 1C:
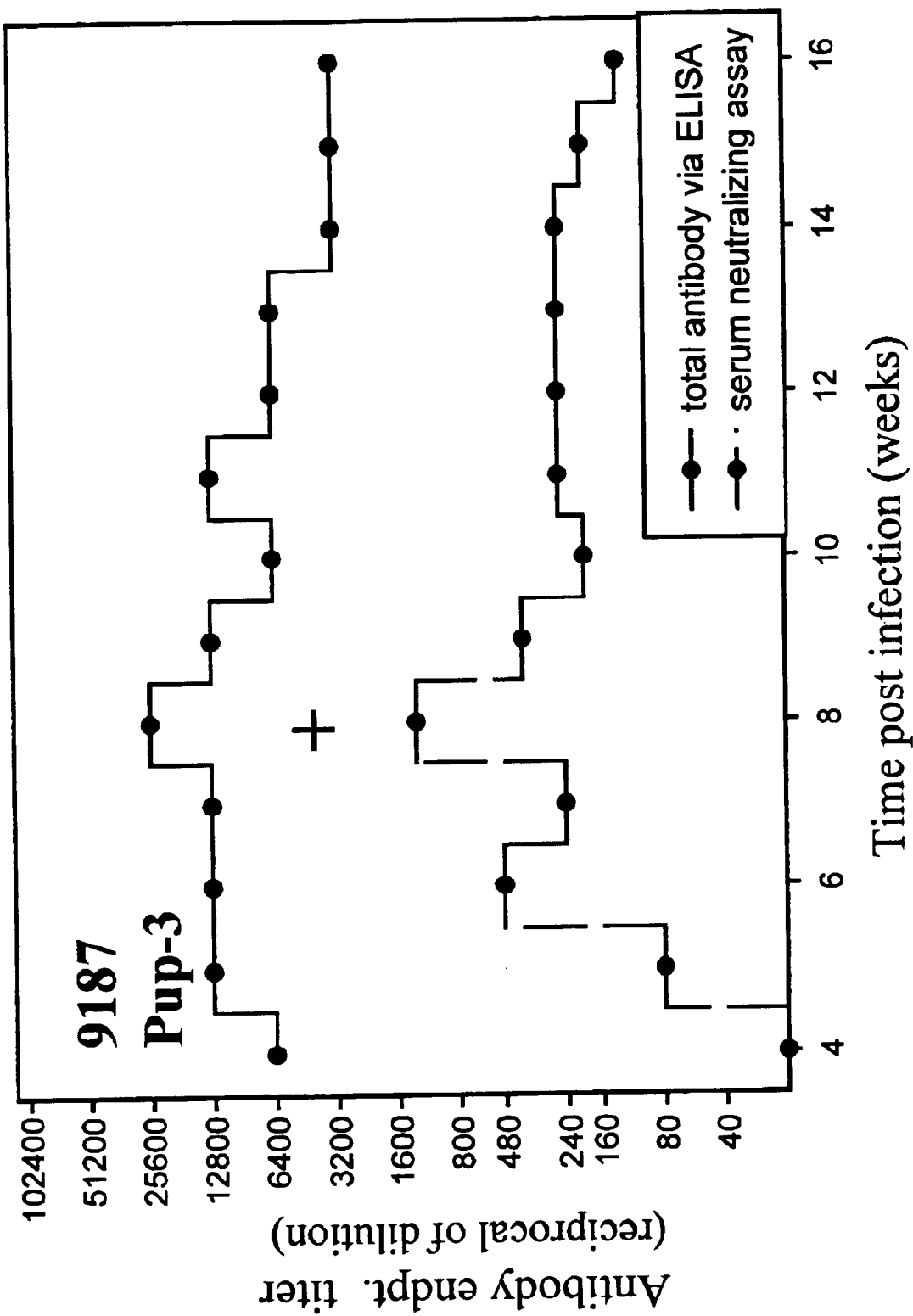
FIG. 1C shows the results from pup-3. The pups were bled each week beginning at 4 weeks and continuing to 16 weeks post inoculation. The titer of total antibody to BVDV antigens was determined by ELISA using cpBVDV-infected cell extracts for antigen capture (solid line). The titer of BVDV neutralizing antibody was determined by serum neutralizing assay (dashed line). Antibody titers were expressed as the reciprocal of the dilution tested.

Titers of serum neutralizing antibody to BVDV were measurable in pups-1 (FIG. 1A) and -2 (FIG. 1B) beginning at 4 weeks post inoculation and in pup-3 (FIG. 1C) at 5 weeks post inoculation. Similar to the pattern for the total antibody response the titer of the neutralizing antibody response tended to increase in pup-1 (FIG. 1A), remain constant in pup-2 (FIG. 1B), and decrease in pup-3 (FIG. 1C). Both the total antibody and serum neutralizing antibody responses were greatest in BVDV-infected pup-1. Serology performed on uninfected control 9203 pups and dams of both liters were negative for antibody toward BVDV throughout the course of this study.

Example 2
Cellular Immune Response to BVDV Antigens

The result of the inoculation of neonate woodchucks and the development of a productive infection were further investigated by monitoring the cellular immune response as an indication of BVDV replication. A cellular immune response to BVDV infection was assayed with peripheral mononuclear blood cells (PMBC) from pups born to dam 9187, collected at weeks 4, 9 and 16 post inoculation with the ncpBVDV (Table I).

TABLE I

Results of peripheral blood mononuclear cell (PBMC) proliferation assay.

| Woodchuck # | 9187 | | |
|---|---|---|---|
| Week | 4 | 9 | 16 |
| mL EDTA/cells (Mio) | <1.0/9.20 | 2.0/3.1 | 5.0/22.3 |
| Cell/Well (×1000) | 50 | 50 | 50 |
| Blank (CPM) | 3142 | 2056 | 2042 |
| Con A 8 µg/mL (SI) | 26.7 | 16.8 | 19.1 |
| SU BVDV − (10.0 µg/mL) | 1.1 | 1.4 | 0.9 |
| SU BVDV − hi (10.0 µg/mL) | 0.8 | 0.9 | 1.0 |
| SU BVDV + (10.0 µg/mL) | 1.1 | 1.3 | 0.8 |
| SU BVDV + hi (10.0 µg/mL) | 0.8 | 1.6 | 0.9 |
| CE BVDV − (10.0 µg/mL) | 1.1 | 1.1 | 0.8 |
| CE BVDV − hi (10.0 µg/mL) | 0.9 | 1.1 | 0.8 |
| CE BVDV + (10.0 µg/mL) | 1.2 | 1.1 | 0.9 |
| CE BVDV + h1 (10.0 µg/mL) | 1.1 | 1.7 | 0.9 |
| CE BVDV #2 + (10.0 µg/mL) | 1.5 | 1.0 | 0.7 |
| CE BVDV #2 + (10.0 µg/mL) | 1.0 | 1.3 | 0.8 |

Neonatal BVDV Infection

| Woodchuck # | 9187-1 | | | 9187-2 | | | 9187-3 | | |
|---|---|---|---|---|---|---|---|---|---|
| Week | 4 | 9 | 16 | 4 | 9 | 16 | 4 | 9 | 16 |
| mL EDTA/cells (Mio) | <1.0/1.20 | 3.0/6.2 | 5.0/16.0 | 1.0/3.05 | 3.0/16.95 | 5.0/26.5 | <1.0/0.70 | 3.0/13.65 | 5.0/16.0 |
| Cell/Well (×1000) | 50 | 50 | 50 | 50 | 50 | 50 | 50 | 50 | 50 |
| Blank (CPM) | 1041 | 874 | 2289 | 772 | 1387 | 1597 | 380 | 1596 | 1507 |
| Con A 8 µg/mL (SI) | 11.6 | 66.7 | 27.3 | 22.6 | 43.6 | 33.1 | 4.7 | 24.3 | 37.1 |
| SU BVDV − (10.0 µg/mL) | — | 1.7 | 0.7 | 1.2 | 1.4 | 1.1 | — | 1.2 | 0.9 |
| SU BVDV − hi (10.0 µg/mL) | 1.4 | 0.0 | 1.3 | 1.2 | 1.3 | 1.5 | 1.3 | 1.0 | 0.8 |
| SU BVDV + (10.0 µg/mL) | — | 0.8 | 2.0 | 1.2 | 2.8 | 1.4 | — | 3.2 | 2.1 |
| SU BVDV + hi (10.0 µg/mL) | 2.3 | 1.5 | 1.9 | 1.2 | 2.4 | 1.2 | 1.6 | 3.6 | 1.8 |
| CE BVDV − (10.0 µg/mL) | — | 1.2 | 0.6 | 1.3 | 1.0 | 1.2 | — | 1.1 | 0.9 |
| CE BVDV − hi (10.0 µg/mL) | 1.3 | 1.2 | 1.1 | 1.3 | 1.1 | 1.9 | — | 1.0 | 1.0 |
| CE BVDV + (10.0 µg/mL) | — | 1.6 | 1.1 | 1.4 | 2.0 | 0.8 | — | 2.4 | 1.0 |
| CE BVDV + h1 (10.0 µg/mL) | 1.1 | 1.4 | 0.8 | 1.3 | 1.8 | 1.8 | — | 2.4 | 0.9 |
| CE BVDV #2 + (10.0 µg/mL) | — | 1.4 | 1.3 | 1.2 | 2.0 | 0.8 | — | 2.1 | 0.7 |
| CE BVDV #2 + (10.0 µg/mL) | 1.3 | 1.7 | 1.0 | 1.0 | 1.6 | 0.9 | — | 2.0 | 1.1 |

SU = Cell supernatant
CE = Cell extract
"−" = uninfected cells
"+" = BVD infected cells
hi = Heat inactivated for 30 min at 70° C.

A cellular immune response to BVDV infection was assayed with peripheral mononuclear blood cells (PMBC) from pups born to dam 9187, collected at weeks 4, 9, and 16 post inoculation with the ncpBVDV. A stimulation index greater than 3.1× above unstimulated control cells was detected in PBMC isolated from pup-3 at 9 weeks post inoculation.

PBMC isolations were poor on 4 week old pups, but no significant stimulation was detected at this time point. A stimulation index greater than 3.1× above unstimulated control cells was detected in PBMC isolated from pup-3 at 9 weeks post inoculation. No significant proliferation was detected in PBMC from BVDV-infected pups at 16 weeks post inoculation. Cellular proliferation in response to BVDV antigens was not detected in PBMC isolated from dam 9187 at any time point.

Example 3
Antibody Response to Specific BVDV Antigens

Figure 2:
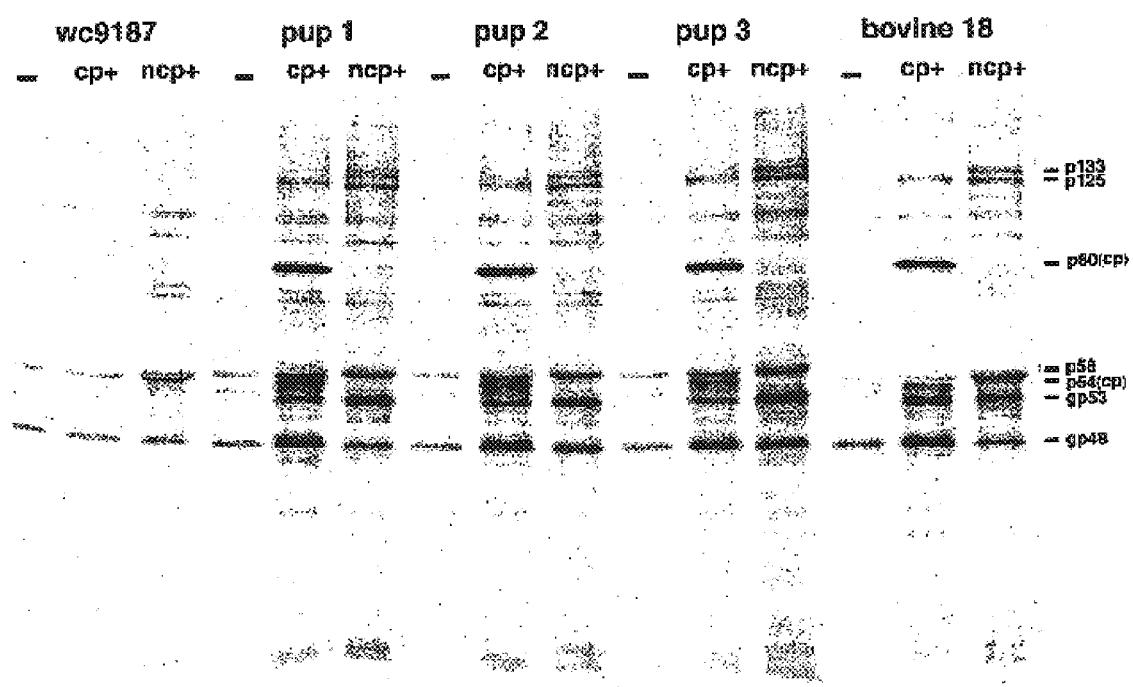
FIG. 2 is an autoradiograph of the immunoprecipitation of BVDV antigens with woodchuck serum obtained after inoculation with BVDV. Serum collected from neonate woodchucks at 6 weeks post inoculation with ncpBVDV was used to precipitate BVDV specific antigens from [$^{35}$S] met-cys labeled bovine cell culture extracts. Woodchuck antibody bound with viral antigen was eluted from protein G beads and separated by 12% SDS-PAGE followed by fluorography to detect proteins by autoradiography on X-ray film. Hyper-immune bovine serum positive for BVDV-antibodies (bovine 18) and woodchuck serum from wc9187 were included as controls to her pups 1, 2 and 3. BVDV neg. cell extract (−) and BVDV pos. cell extract (cytopathic NADL: cp+, noncytopathic NY-1: ncp+) were precipitated as noted. BVDV specific proteins are labeled on the right.

The determination that the immune responses in neonate woodchucks were associated with BVDV infections was established by showing antibody specific to viral nonstructural proteins, indicative of active viral replication. Immunoprecipitation of cpBVDV-infected cell cultures with woodchuck serum collected after inoculation demonstrated reaction to viral antigens (FIG. 2). Serum collected from pups inoculated with ncpBVDV precipitated the viral envelope proteins gp48 (E0) and gp53 (E2) as early as 4 weeks post infection. Additionally, the viral nonstructural proteins p125 (NS2/3), p80 (NS3), p133 (NS5a/b), and p58 (NS5a) were precipitated. Serum collected from uninfected pups and the dams of each liter failed to precipitate BVDV specific proteins.

Isolation of infectious virus from neonate woodchucks infected with BVDV. The re-isolation of infectious virus from BVDV-infected neonate woodchucks would establish the complete reproductive viral cycle. PBMC were isolated from BVDV-infected pups beginning 4 weeks after infection and assayed for the presence of virus on susceptible bovine cell lines. Infectious virus was re-isolated from the PBMC of BVDV-infected pup-3 at 7 weeks post infection. Virus was not isolated from the PBMC of the other animals at any time point.

Fresh tissues including liver, spleen and kidney were collected at necropsy 16 weeks post infection and processed for the isolation of infectious virus. Infectious virus was recovered from the kidney of BVDV-infected pup-1. Serologic analysis (Corpai, W. V. et al. (1990) Am. J. Vet. Res. 51: 1388–1394) on recovered virus demonstrated these isolates were derived from the NY-1 isolate of BVDV used for inoculation, and not a laboratory isolate possibly contaminating the assays.

Example 4
Liver Enzyme Activity in Neonate Woodchucks

Figure 3B:
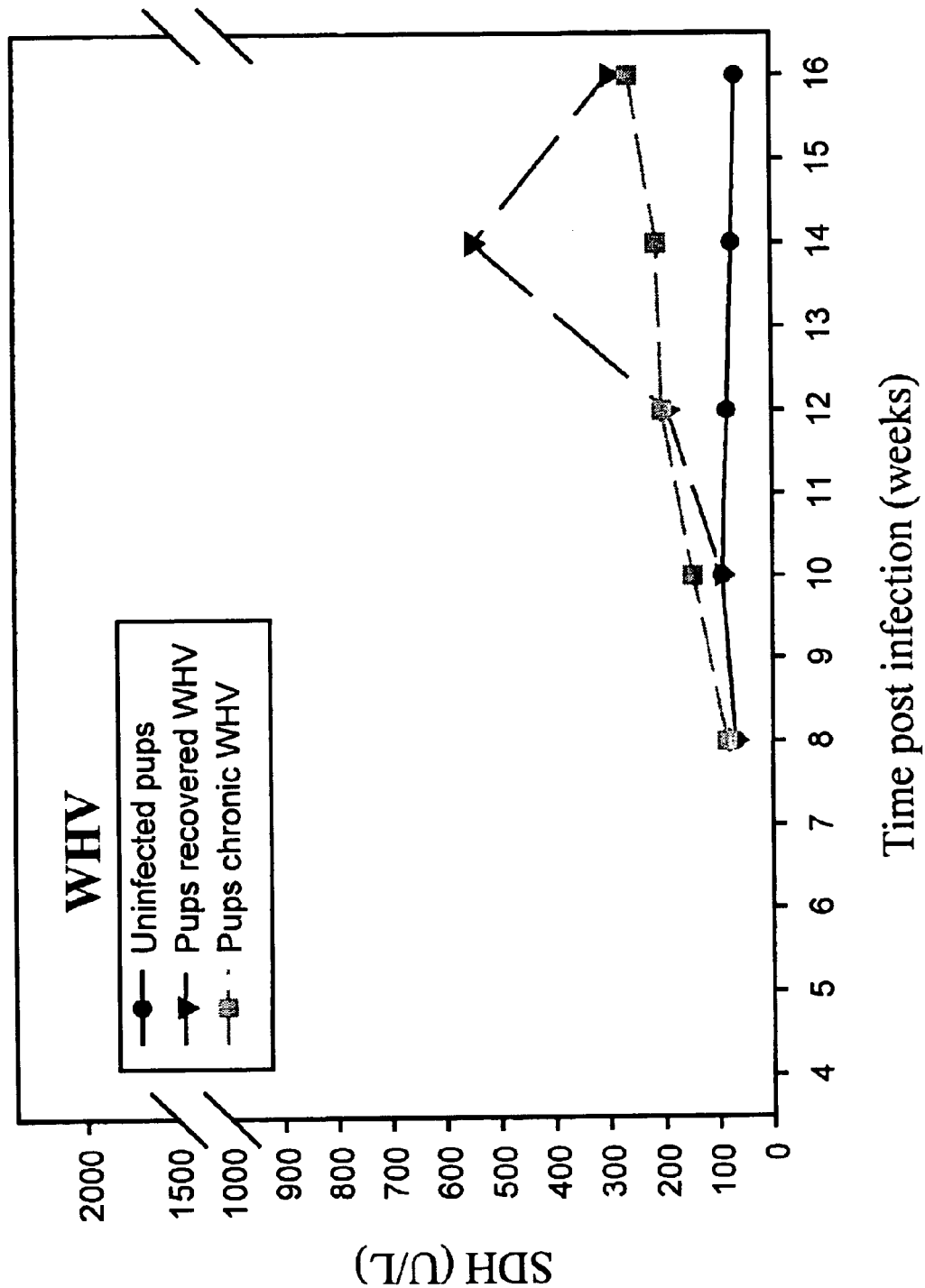
FIG. 3B illustrates SDH activity in uninfected pups, pups recovered from WHV, and pups with chronic WHV infection.
Figure 3C:
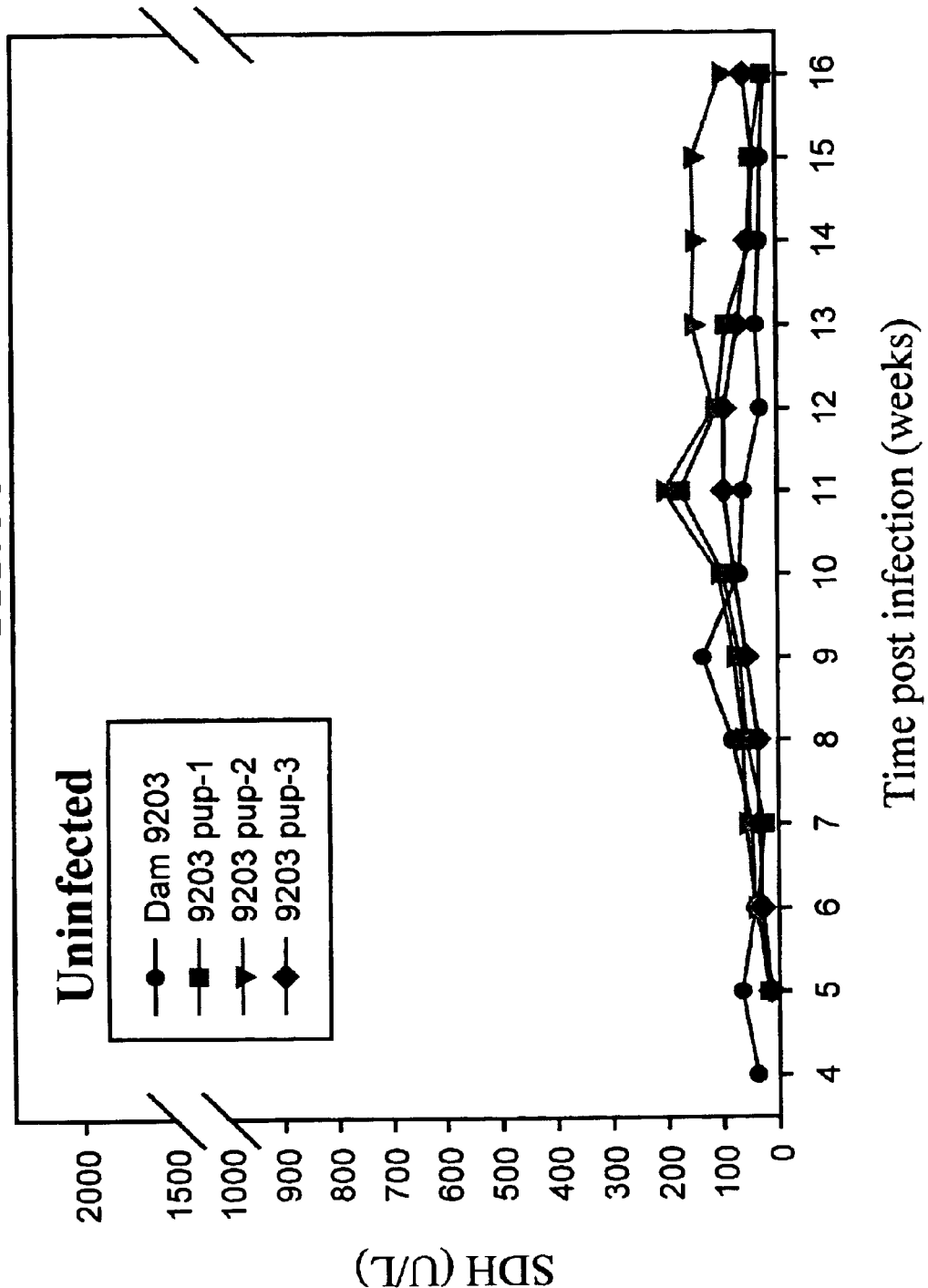
FIG. 3C) were bled each week beginning at 4 weeks and continuing to 16 weeks post inoculation. Serum levels of sorbitol dehydrogenase (SDH) were determined. Enzyme activity was plotted as units per liter on a linear scale (U/L). Increase in liver enzyme activity in the serum of dams of each litter was not observed.

The association between BVDV infection of neonate woodchucks and development of disease was investigated by monitoring aminotransferase (ALT), aspartate aminotransferase (AST), and sorbital dehydrogenase (SDH) activity as an indication of liver pathology. There were elevations in liver enzyme activity detected in the serum of pups born to dam 9187, which were infected with BVDV (FIG. 3A). Serum SDH activity increased in pup-2 and increased substantially in pup-3 beginning at 9 weeks post infection. SDH activity did not elevate significantly in BVDV-infected pup-1 when compared to uninfected pups and the dams of each liter. The marked SDH elevation in BVDV-infected pup-3 was followed by significant elevation in both ALT and AST activity at 15 weeks post infection. Enzyme activity began to decrease in BVDV-infected pups at 16 weeks post infection.

Example 5
Histologic Features of Neonate Woodchucks Infected with BVDV

Figure 4:
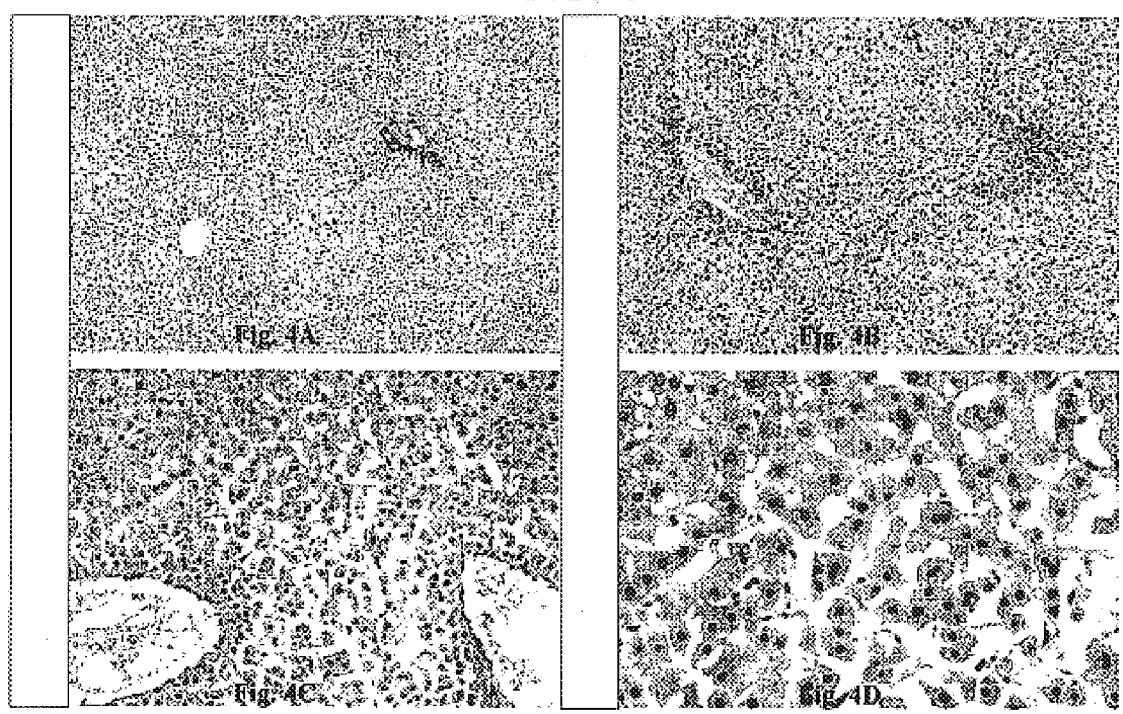
FIG. 4 is a panel of micrographs showing histologic features of liver in neonate woodchucks after inoculation with BVDV. Liver samples taken of neonate woodchucks at 16 weeks post BVDV-infection and from uninfected controls were fixed in formalin and stained with hemotoxylin and eosin. (A) Liver of uninfected control wc9203 pup-1. Uniform appearance of the hepatocytes around portal tract (upper right) and central vein (lower left). (B-D) Liver of BVDV-infected wc9187 pup-3. (B) Pericentral hepatocytes showing compact and eosinophilic cytoplasm and nuclei with condensed chromatin. (C) Pronounced necrobiotic changes in hepatocytes around central veins with distention of veins and sinusoids. (D) Signs of cell injury and death without accompanying inflammatory infiltration. Magnification of panels A and B ×50, C ×100 and D ×200.

The association between BVDV infection of neonate woodchucks and development of disease was investigated by examining tissue of several organs for pathologic changes. No macroscopic alterations were noted. Microscopically, there were predominately necrobiotic changes in the liver of pups born to dam 9187, which were inoculated with ncpBVDV (FIG. 4). There were subtle changes in the liver of pup-1. Single or small groups of hepatocytes, mainly in the periportal region but occasionally centrally, showed condensed more eosinophilic cytoplasm and had vesicular nuclei, or nuclei with condensed chromatin up to pyknosis indicative of cell injury. No inflammatory reaction or infiltration was observed in these regions. The changes in the liver of pup-2 observed were minimal if at all. Single hepatocytes exhibited condensed and eosinophilic cytoplasm scattered mosaically in some periportal regions. Most extensive necrobiotic changes were observed in the liver of pup-3. Rows of 5 to 10 hepatocytes thick around numerous central veins showed signs of cell injury and death with coagulative necrosis of the cytoplasm and pyknotic nuclei. They were smaller in size and detached leading to enlargement of the lumen of the central veins and the surrounding sinusoids. The severity of the alterations decreased with distance from the central vein. No inflammatory reaction was seen.

Figure 5:
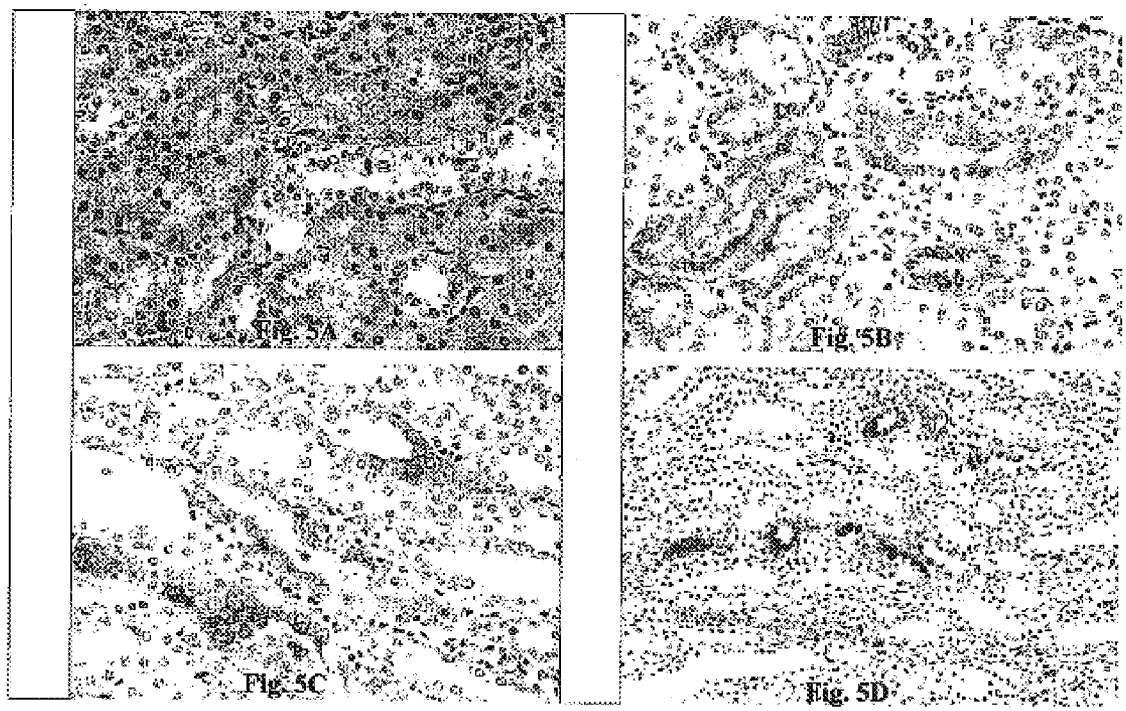
FIG. 5 is panel of micrographs showing immunohistologic staining for BVDV-antigens in kidney of neonate woodchucks after inoculation with BVDV. Kidney tissue taken 16 weeks post BVDV-infection of neonate woodchucks were fixed in formalin and stained with a mouse monoclonal antibody to BVDV antigens. (A) Kidney of wc9187 pup-1 stained with hemotoxylin and eosin showing few tubules have distended lumen and necrobiotic changes of the epithelium. (B) Immunostaining of parallel sections showing granular cytoplasmic staining of the epithelial cells of some of the tubules. (C) Immunostaining of both altered and visibly unchanged tubules. (D) Various intensity of BVDV antigen expression in epithelia of different tubules and even in cells of the same tubule. Magnification panels A–C ×40 and D ×20.

Histologic lesions were detected in the kidneys of BVDV-infected pups (FIG. 5). Patchy scattered in the cortex of the kidney of pup-1 were distal convoluted tubules with distended lumen, uneven luminal margin and saw-like projections. A pattern of variable nuclear distribution on the basal membrane with piling up and sloughing off was observed. Some of the epithelial cells were with compact, more eosinophilic cytoplasm, condensed nuclear chromatin or pyknosis. No inflammatory reaction or infiltration around these tubules was evident. Single epithelial cells with pyknotic nuclei and necrobiosis were observed in some proximal tubules in the kidney of pup-2. In the kidney of pup-3 minimal changes in primary convoluted tubules and a site of lymphoid cell interstitial infiltration were observed.

Uninfected pups of dam 9203 of the same age and upkeep showed no pathological changes in the tissues examined. Dam 9187 showed no significant changes except for foci of extramedular hematopoiesis in portal fields and in some sinusoids of the liver, findings not observed in dam 9203. No significant findings in the intestine, lymph nodes, gonads or pancreas were noted.

Immunohistologic detection of BVDV antigens. The determination that pathologic changes in neonate woodchucks were associated with BVDV infections was supported by detecting BVDV antigens in the kidney of pup-1, indicative of replicating virus. Positive immunohistologic staining with anti-BVDV serum was observed in some tubules scattered in the cortex of the kidney while the glomeruli were negative (FIG. 5). The staining was cytoplasmic and granular, showing various intensity in different tubules or even in cells of the same tubule. Both tubules that appeared morphologically unchanged and tubules with distended lumen and irregular lining were labeled. Consecutive sections of the kidney stained with H&E and immunohistochemically allowed the direct linking of individual epithelial cells of the tubules to the site of positive viral antigen staining. The specific immunostaining was consistently observed in the 3 samples of the kidney of pup-1 examined. All other tissues of pup-1 and of other inoculated and control pups and mothers were negative immunohistochemically. This result corroborated the positive isolation of infectious BVDV from the kidney sample taken from pup-1 at necropsy 16 weeks post inoculation.

The infection of neonate woodchucks with WHV results in the establishment of a persistent WHV-carrier state. This may be attributed to immune modulating mechanisms in the developing pup, which allows the virus to establish a persistent infection (Chisari, F. V., and Ferrari, C. (1997) Viral hepatitis. In: Viral Pathogenesis. Ed: Nathanson, N., et al. Lippincott-Raven Publishers, Philadelphia, 1997: 745–778). Mother to infant transmission of Flaviviruses is an established fact, and similar immune evasive mechanisms may be operational (Meyers, G., and Thiel, H. -J. (1996) Adv. In Virus Res., 47: 53–118; Cerney, A., and Chisari, F. (1999) Hepatology, 30: 595–601).

In the experimental oral or nasal BVDV inoculation of calves, virus can be isolated from the blood within the first few days of infection (Liess, B. Bovine viral diarrhea virus. In: Virus infections of ruminants. B. Morein and Z. Dinter eds: Elsevier Science Ltd, 1990). Infectivity can be detected in leukocytes in the presence of demonstrable antibody as well. Mononuclear leukocytes are considered one target organ for BVDV replication (Beilefeldt-Ohmann, H. et al. (1987) J. Gen. Virol. 68: 1971–1982), but viral spread occurs during viremia from the site of primary replication.

A noncytopathogenic isolate of BVDV, NY-1, which is considered highly virulent for its capacity to elicit disease symptoms in cattle was tested in colony bred, day old woodchucks. A positive isolation of BVDV was obtained on PBMC isolated from BVDV-infected pup-3 at 7 weeks post inoculation. The recovery of infectious virus suggested BVDV had replicated in some tissue, although the failure to isolate BVDV at earlier time points suggested PBMC were not the primary targets. Infectious virus was isolated from a homogenate of kidney tissue taken from BVDV-infected pup-1 at necropsy 16 weeks post inoculation. This result suggested that virus may reside in the kidney. Serologic evaluation confirmed these isolates were derived from the starting inoculum and not a result of laboratory contamination. The recovery of infectious virus from two of three animals, from different tissues, and more than 2 months after inoculation demonstrated neonate woodchucks were permissive to infection with ncpBVDV.

BVDV usually induces lifelong immunity and the detection of neutralizing antibody reflects this fact. In cattle from which virus can be isolated from the blood, serum neutralizing antibody titers below 1:5 are an indication of a persistent infection (Liess, B. Bovine viral diarrhea virus. In: Virus infections of ruminants. B. Morein and Z. Dinter eds: Elsevier Science Ltd, 1990). In persistently infected calves virus can be isolated from the PBMC even in the presence of neutralizing antibody (Liess, B. Bovine viral diarrhea virus. In: Virus infections of ruminants. B. Morein and Z. Dinter eds: Elsevier Science Ltd, 1990). These antibodies may come from maternal antibody in colostrum or may be specific to a heterologous strain. Serum neutralizing antibodies to BVDV were detected in the serum of BVDV-infected pup-1 and -2 at the earliest time point sampled 4 weeks post infection. An increase in antibody titer was demonstrated in BVDV-infected pup-1 from which infectious virus was recovered from kidney tissue at 16 weeks post infection. This data indicated that active viral expression was responsible for the stimulation of the immune response in BVDV-infected pup-1. In the serum of BVDV-infected pup-3, neutralizing antibody was not demonstrated at 4 weeks post infection. Antibody titers did increase 5 to 8 weeks post infection of BVDV-infected pup-3, but then diminished with time. Infectious BVDV was re-isolated from the PBMC of pup-3 at 7 weeks post infection. Additionally, significant PBMC proliferation in response to viral antigens was demonstrated for peripheral lymphocytes isolated from BVDV-infected pup-3 at 9 weeks post infection. However, it was not determined whether a decrease in any specific lymphocyte population accounted for the decrease in antibody titers in BVDV-infected pup-3. Total antibody to BVDV, detected by ELISA, was not demonstrated in any of the uninfected control pups and not in either dam of the woodchuck litters. This result indicated that maternal transfer of antibody was not responsible for the immune responses demonstrated in the neonates, nor was there transmission of infectious virus from pup to mother or from extraneous sources.

Clinical manifestations of BVDV infections are related to age and immunologic status of the host, and biotype of the inoculating virus (Corapi, W. V. et al. (1989) J. Virol., 63:3934–3943). Additionally, severe disease is associated with infection with both noncytopathogenic and cytopathogenic isolates of BVDV. Acute hepatic damage was indicated by an increase in SDH activity found in the serum of BVDV-infected pups-2 and -3. The onset of enzyme activity occurred at a point in which infectious virus was isolated from the PBMC of BVDV-infected pup-3. The severity of the liver enzyme activity appeared to inversely correlate with the antibody response.

Histologically, similar trends were apparent. Necrobiotic changes in the liver were minimal in BVDV-infected pup-2, moderate pathologic changes observed in pup-1, and the most severe hepatic damage was observed in pup-3. The morphologic alterations in the liver of the inoculated pups were definitely associated with BVDV infection as no such changes were observed in the control pups and in the mothers. The signs of moderate or advanced injury and death of hepatocytes was not accompanied by inflammatory infiltration or manifestation of portal or lobular hepatitis.

Reference has been made to involvement of the kidney during the pathogenesis of disease in persistently BVDV-infected cattle (Liess, B. Bovine viral diarrhea virus. In: Virus infections of ruminants. B. Morein and Z. Dinter eds: Elsevier Science Ltd, 1990) and been used for immunodiagnostic purposes (Thur, B. et al. (1997) Am. J. Vet. Res., 58(12): 1371–1375). Microscopic lesions, thickening of the glomerular basement membrane with eosinophilic material, and maesangial cells were reported by Cutlip et al (Cutlip, R. C. et al. (1980) Am. J. Vet. Res., 41(12): 1938–194). Further examination by immunofluorescence revealed viral antigen to be localized intracytoplasmic in mesangial and endothelial cells of glomeruli, and appeared as a granular pattern in the glomerular basement membrane.

In contrast, observations on the kidney specimens from BVDV-infected pup-1 revealed necrobiotic changes in the epithelium of distal convoluted tubules in the cortex with uneven luminal margin and size and uninvolved glomeruli. The specificity of the BVDV immunostaining was supported by the negative controls, the reproducible staining results in different kidney samples and the fact that positive labeling was observed both in altered and visibly unchanged tubules. An immune-mediated reaction with deposition of viral antigens along the basement membrane did not appear to be responsible for these observations. This data combined with the recovery of infectious virus from identical tissue, 16 weeks post infection, indicated a possible active site of viral replication in the woodchuck.

The inoculation of neonate woodchucks with ncpBVDV has yielded much information toward its genesis as a model to study the pathogenesis of HCV infection of humans. The viremic phase after infection was presumed to be less than 4 weeks in woodchucks versus 3–5 days in cattle. It has been reported that viral RNA can be detected as early as 2 days post infection upon experimental HCV infection of the chimpanzee (Negro, F. et al. (1992) Proc. Natl. Acad. Sci. USA, 89: 2247–2251). The development of an immune response, specifically a serum neutralizing antibody response, occurred within 4 weeks after infection in the woodchuck, versus 2 weeks in cattle. The recovery of infectious virus from woodchuck PBMC in the presence of antibody has been similarly reported in cattle (Liess, B. Bovine viral diarrhea virus. In: Virus infections of ruminants. B. Morein and Z. Dinter eds: Elsevier Science Ltd, 1990). A contributing factor to the pathogenesis of chronic HCV infections is the finding of infectious virus in the presence of an antibody response (Bassett, S. E. et al. (1999) J. Virol., 72(4): 2589–2599). Clinical symptoms of infection in the woodchuck were elevated liver enzymes, findings characteristic of HCV infections. Histologically, necrobiotic changes in the liver and kidney were identified in BVDV-infected woodchucks. Similar histologic changes were reported in BVDV infections of cattle (Cutlip, R. C. et al. (1980) Am. J. Vet. Res., 41(12): 1938–1941).

EXAMPLES

Methods and Materials (Examples 6–12)

The data described in the following examples 6–12 was obtained using the following Methods and Materials.

Characterization of Woodchuck Hepatocytes Infected with BVDV

The permissive state of woodchuck hepatocytes to BVDV infection was investigated. After inoculation with cpBVDV in both woodchuck primary hepatocyte cultures and woodchuck hepatic cell lines, the cytopathic effects and viral production were examined. Replication and expression of cpBVDV in primary hepatocyte cultures and in hepatic cell lines were compared to that in cells of bovine origin. Further, these woodchuck hepatic cells and BVDV were assessed as an in vitro assay to screen antivirals using compounds known to be effective against chronic HCV infection of humans.

Cells cultures: The bovine uterine cell line, designated NCL, was generated via immortalization of primary bovine uterine cells with the SV40 large T antigen oncogene (pSV3neo; ATCC cat.# 37150) by a previously described procedure (Dobrinski, I. et al. (1999) Theriogenology, 52: 875–885). The woodchuck hepatic cell line WCH-8 was derived by treatment of primary woodchuck hepatocytes with lipopolysaccharide. Primary woodchuck hepatocyte cultures were maintained by a previously described procedure (Jacob, J. R. et al. (1994) Exp. Cell Res., 212:42–38). Bovine cell lines were maintained in MEM-E medium (LifeTechnologies, Grand Island, N.Y.) containing 10% bovine serum [Atlantic Biologics; negative for BVD contamination (gamma irradiated) and free of antibody against BVD] supplemented with 10 mM HEPES, gentimicin (50 ug/mL), and streptimicin and penicillin (LifeTechnologies). Cell lines were incubated in a humid atmosphere of 5% $CO_2$ at 37° C. Cell lines were passaged by dissociation of the cell monolayer with a solution of trypsin-EDTA (LifeTechnologies), diluted in culture medium and split 1:5 to new culture flasks.

BVDV stocks and titration: The cytopathogenic NADL isolate of BVDV (cpBVDV) was used for the purposes of this study. A viral stock was made by freeze-thaw of a bovine testicular cell line 5 days after infection with cpBVDV. Virus propagated in bovine cells and woodchuck cell cultures was tittered in NCL cells by measuring cytopathic effects (CPE). NCL cells grown to confluence, were passaged to 96 well microtiter plates at a density of $2\times10^4$ cells/well ($5\times10^5/cm^2$) and incubated for one hour to allow cell attachment. After attachment, cell cultures were inoculated with serially diluted tissue culture supernatant samples. The endpoint BVDV titer was taken as the reciprocal of the last dilution in which cells were killed 5 days post-infection in one of three triplicate wells, assayed by methylene blue staining.

Methylene blue assay: A quantitative measure of cell numbers was obtained through reading the absorbance of methylene blue (Sigma, St. Louis, Mo.) uptake by viable cells. Briefly, three days after infection of cells with cpBVDV, cultures were rinsed with phosphate buffered saline (PBS; Life Technologies) followed by fixation in a Hanks balanced salt solution (HBSS; LifeTechnologies) consisting of 1.25% glutaraldehyde (Fisher Scientific, Fair Lawn, N.J.) and 0.06% methylene blue (Sigma), for 1 hour at 37° C. The methylene blue solution was removed from the cultures and the plates rinsed in several volumes of $H_2O$. The culture plates were allowed to air dry briefly, followed by elution of the methylene blue stain from the fixed cells by incubation in a solution of PBS consisting of 50% ethanol and 1% acetic acid for 1 hour with agitation at room temperature. The absorbance of the methylene blue in solution was measured using an ELISA plate reader (Model EL311; Bio-Tek instruments Inc., Winooski, Vt.) with a light filter setting at 630 nm. A standard curve was established for each cell line relating absorbance with cell numbers. A linear regression was used for the calculation of cell numbers for each experimental data point (dilution, titer or antiviral concentration), and are the average of three wells per experimental treatment.

Immunologic analysis: Immunoblot assay was performed by a modification of a previously described procedure (Jacob, J. R. (1996) Carcinogenesis, 17(4):631–636). Briefly, cell homogenates were prepared and proteins separated by sodium dodecyl sulfate-polyacrylamide gel electrophoresis (SDS-PAGE). After electrotransfer of proteins to nylon membranes (NEN-DuPont, Boston, Mass.) the mouse monoclonal antibody MAB 10.2.24, specific to the BVDV p80 (NS3) protein, was used at a dilution of 1:5,000 (Haines, D. M. (1992) Vet. Path., 29:27–32). Immunoprecipitation was performed by a modification of a previously described procedure (Jacob, J. R. et al. (1994) Exp. Cell Res., 212:42–38). Briefly, cell extracts were made of uninfected and BVDV-infected woodchuck and bovine cell cultures labeled with [$^{35}$S]met-cys (ICN, Costa Mesa, Calif.), followed by precipitation with hyperimmune bovine serum (cow18). Bovine antibody bound with viral antigen was eluted from protein G beads and separated by 12% SDS-PAGE followed by fluorography to detect proteins by autoradiography on X-ray film. Immunofluorescence was performed by a modification of a previously described procedure (Corapi, W. V. (1989) J. Virol., 63: 3934–3943). Briefly, uninfected and BVDV-infected woodchuck and bovine cell cultures grown on glass coverslips were fixed in acetone and stained with MAB 10.2.24 (1:250 dilution) followed by incubation with a secondary antibody; goat anti-mouse Ig conjugated to FITC (dilution 1:50). Cells were observed and photographed under epifluorescence (wide blue band) by phase-contrast microscopy.

cDNA probes and hybridizations: A BVDV specific probe was generated from the 1.85 kb EcoRI/BamHI fragment of pc7 (NS3 region of BVDV strain SD-1: Rubin Donis, Univ. Nebraska) by random primed DNA synthesis incorporating [$\alpha^{32}$P]dCTP (NEN-DuPont). Hybridization was performed by a previous described procedure (Jacob, J. R. (1996) Carcinogenesis, 17(4):631–636). Briefly, total cellular RNA was isolated by lysis of cell monolayers with a solution of phenol/guanidium-HCl (Trizol, Life Technologies) and RNA extracted as recommended by the manufacturer. RNA was separated by denaturing agarose gel electrophoresis and transferred to nylon membranes followed by hybridization. Image analysis was performed using a Phosphor-Imager 830 (Molecular Dynamics, Sunnyvale, Calif.).

Antiviral assay: A lyophilized form of Ribavirin (Virazole$^R$; Viratek, Inc., Covina, Calif.) was dissolved in H$_2$O to a yield a stock concentration of 100 mM and serially diluted two fold in culture medium prior to testing over a range of 100–0.049 μM. Ribavirin was evaluated in woodchuck WCH-8 cells and in bovine NCL cells in a 96 well format using the methylene blue assay to measure cell viability. The medium was replenished daily with drug and the antiviral effect, cytotoxicity, and reduction in viral yield determined after three days of treatment. The effects of Ribavirin on BVDV-infected woodchuck primary hepatocytes were assayed in 24 well format using a nonradioactive cytotoxicity assay (CytoTox96$^R$; Promega, Madison, Wis.) to measure cell killing.

Cell killing due to cpBVDV infection and drug cytotoxicity was calculated for each experimental data point and plotted. Regression analysis (curve fitting) was performed with SigmaPlot4.0 (Jandel Sci, San Rafael, Calif.) using the Regression Wizard library of equations that best fit the collected data. A drug concentration sufficient to inhibit 50% of viral induced cell killing ($_{ck}EC_{50}$) was determined using a peak, log normal, 4 parameter equation. A drug concentration which killed 50% of uninfected cells ($CC_{50}$) and a drug concentration which reduced viral titers by 90% ($_{t}EC_{90}$) was determined using a sigmoid, logistic, 4 parameter equation. A selectivity index (SI) was determined as the $CC_{50}/EC_{90}$ ratio.

Example 6
BVDV Infection of Woodchuck Hepatic Cells

Figure 6:
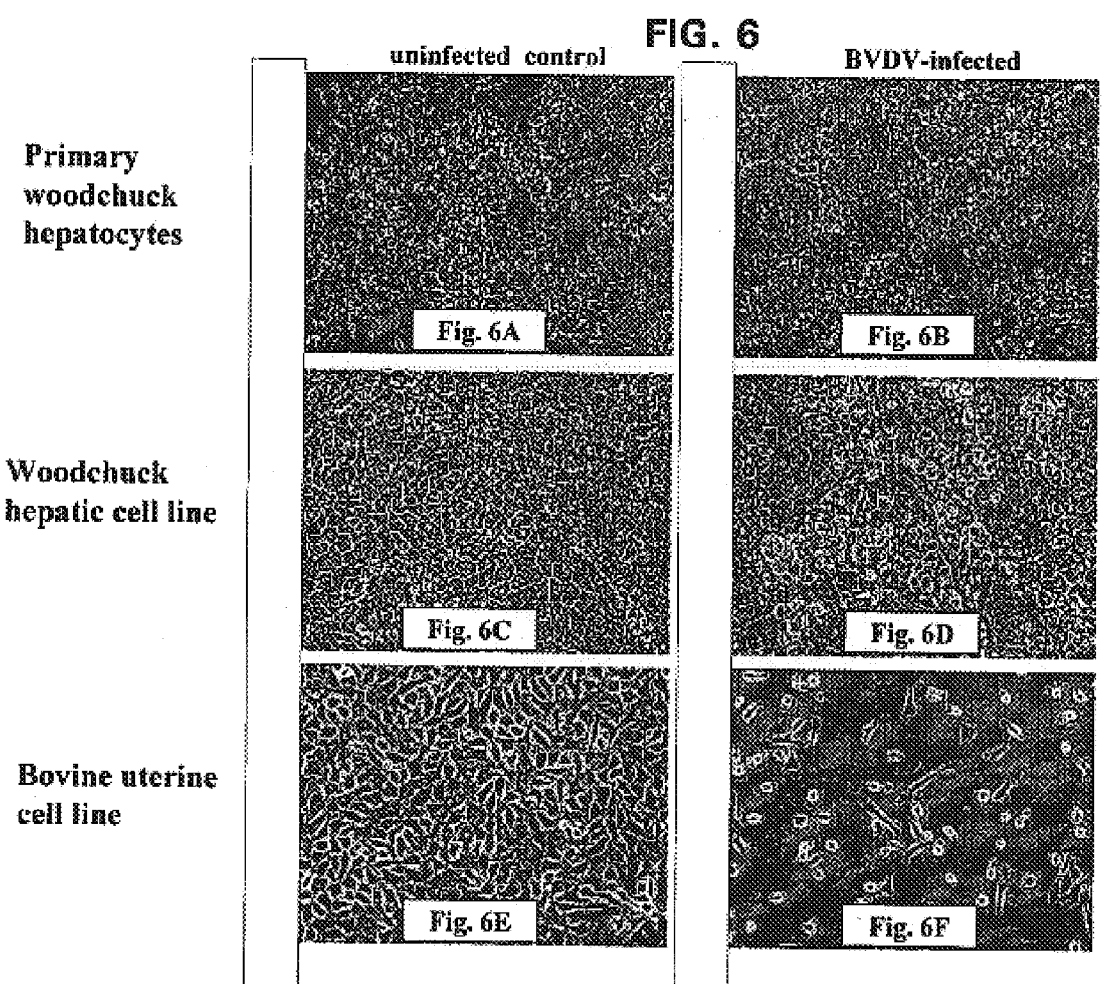
FIG. 6 are phase-contrast photomicrographs of the cytopathic effects (CPE) observed in woodchuck hepatocytes after inoculation with cpBVDV. Woodchuck primary hepatocytes (A, B), hepatic WCH-8 (C, D) and bovine NCL (E, F) cells were cultured and either mock infected (A, C, and E) or inoculated with the cytopathogenic NADL isolate of BVDV (B, D and F). CPE were not observed at week 3 post infection (p.i.) of woodchuck primary hepatocytes (B) compared to uninfected, control cultures (A). CPE were observed at week 1 p.i. of woodchuck WCH-8 cells evidenced by vacuolated cells with condensed nuclei (D), and observed at day 2 p.i. of bovine NCL cells evidenced by cell rounding and loss of monolayer (F) compared to uninfected controls (C and E, respectively).

One characteristic of cpBVDV infection of permissive cells is the development of CPE. The cytopathogenic NADL isolate of BVDV was used at a multiplicity of infection (m.o.i.) of 1 to inoculate woodchuck primary hepatocyte cultures and WCH-8 cells. Evidence of CPE was not readily apparent for over 1 month in BVDV-infected woodchuck primary hepatocyte cultures (FIGS. 6A&B). However, CPE were observed five days post-infection of WCH-8 cultures (FIGS. 6C&D). The most notable changes in cellular appearance were the presence of highly vacuolated cells in comparison to uninfected control cultures. Definitive signs of CPE were observed at two weeks post-infection marked by the degeneration of the cell monolayer in comparison to uninfected control cultures. Infection at a m.o.i. of 0.01 with cpBVDV led to CPE two days post-infection of bovine NCL cells resulting in complete cell killing (FIGS. 6E&F).

Example 7
Propagation of BVDV in Woodchuck Hepatic Cells

Figure 7:
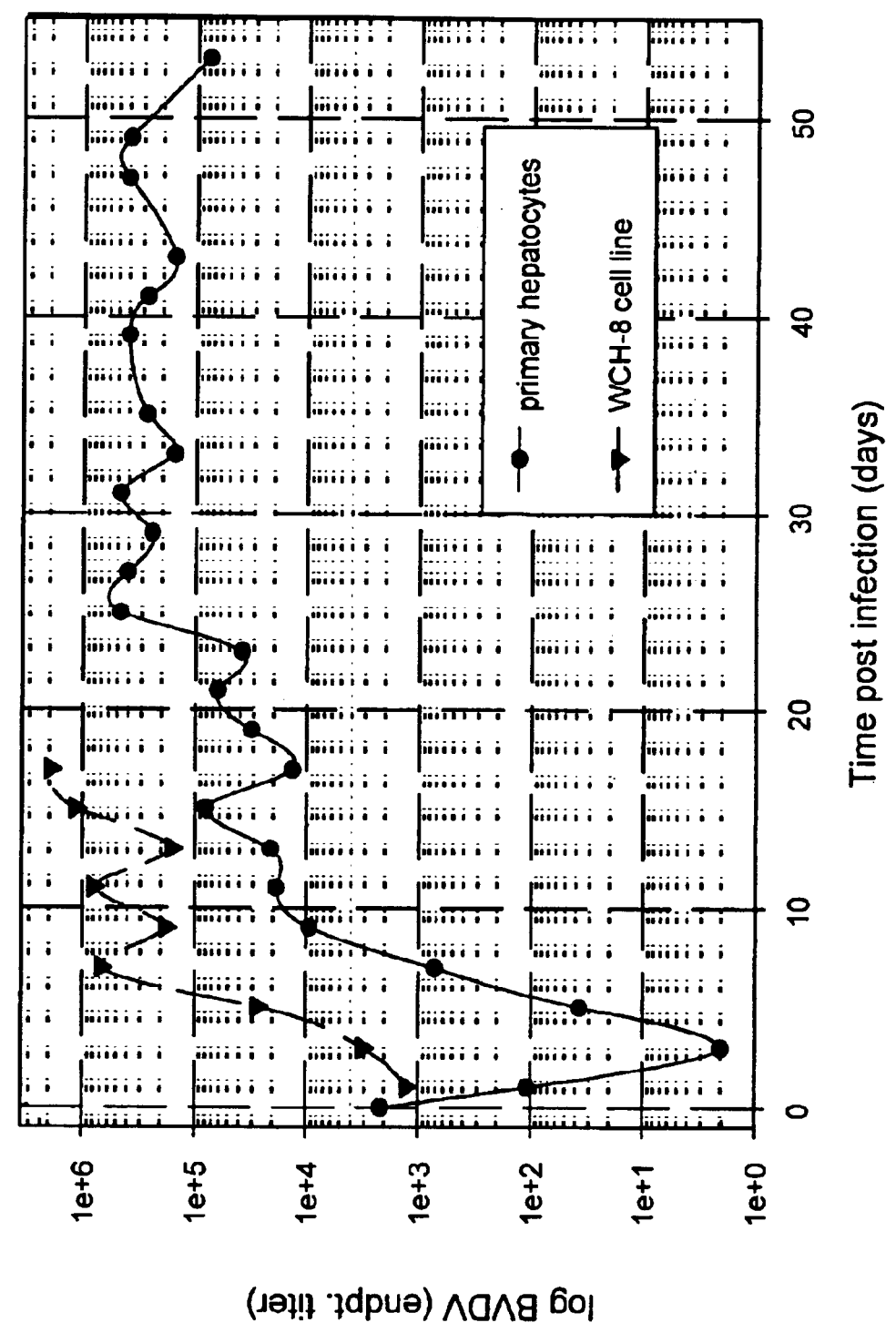

A complete reproductive viral cycle leading to the maturation of infectious virions was examined in woodchuck hepatocyte cultures. The recovery of infectious cpBVDV in the tissue culture supernatant after inoculation with cpBVDV of woodchuck primary hepatocytes and WHC-8 cells was assayed in the bovine NCL cell line. Viral titers were determined for tissue culture medium collected at two-day intervals after cpBVDV infection of woodchuck hepatocyte cultures (FIG. 7). Titers of BVDV found in the culture media increased progressively over a two week period and viral titers approached 1×10$^5$ TCID/mL at 1 month post-infection, without apparent CPE, of woodchuck primary hepatocyte cultures (FIG. 7). Titers of BVDV increased in the culture media 3 days post-infection and approached 2×10$^6$ TCID/mL by 11 days post-infection of WHC-8 cells (FIG. 7). The decline in BVDV titers 13 to 15 days post-infection was reflective on the loss of WCH-8 cells due to increased CPE. Titers of BVDV detected on day 1 post infection was representative of non-bound virus from the inocula.

Example 8
Genomic BVDV RNA in Woodchuck Hepatic Cells

Figure 8:
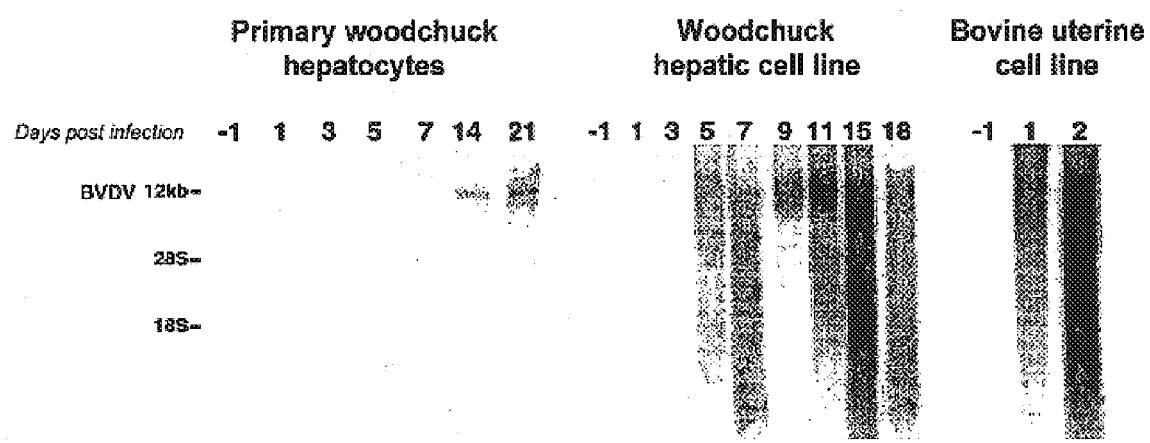
FIG. 8 illustrates BVDV genomic RNA synthesized in woodchuck hepatocytes after inoculation with cpBVDV. Woodchuck primary hepatocytes (A), hepatic WCH-8 (B) and bovine NCL cells (C) were cultured and inoculated with the cytopathogenic NADL isolate of BVDV (cpBVDV). RNA extracts were made at the indicated days post infection (p.i.) and analyzed by nucleic acid hybridization using a probe specific to the NS3 gene of BVDV. Genomic sized BVDV RNA (>12 kb) was detected in extracts beginning day 7 p.i. of primary hepatocytes (A), day 3 p.i. of hepatic WCH-8 cells (B), and day 1 p.i. of bovine NCL cells. The observed CPE coincided with the degradation of BVDV genomic RNA and cellular ribosomes in WCH-8 and NCL cells (B and C). The lack of CPE were indicated by the intact ribosomal RNA observed in extracts of primary hepatocytes and uninfected cells (A; and days −1).

A contributing factor toward CPE due to cpBVDV infection of permissive cells may be the generation of defective particles. Total RNA extracted from BVDV-infected woodchuck primary hepatocytes and WCH-8 cells was examined by nucleic acid hybridization to assess the replicative state of BVDV during the course of infection (FIG. 8A). Genomic BVDV RNA was detected as early as day 5 and continuing to day 35 post-infection in extracts of woodchuck primary hepatocytes (FIG. 8). The quantity of genomic BVDV RNA was less than that found in bovine NCL cells and degeneration of RNA, based upon the integrity of the ribosomal RNA, was not apparent in the hepatocyte cultures.

Genomic BVDV RNA was detected beginning at day 3 and increasing to day 11 post-infection, followed by a decline thereafter, in extracts of WCH-8 cells (FIG. 8B). The mobility of the genomic BVDV RNA found in WCH-8 cells was similar in size and quantity to that detected 1 day post-infection in RNA extracts of NCL cells (FIG. 8C). Sub-genomic sized BVDV RNA was not detected in these extracts. Severe degeneration of RNA, based upon the integrity of ribosomal RNA, was observed within 5 days post-infection which accompanied the onset of CPE in WCH-8 cells, similar to that observed in NCL cells.

Example 9
Processing of p80 (NS3) in Woodchuck Hepatic Cells

Figure 9:
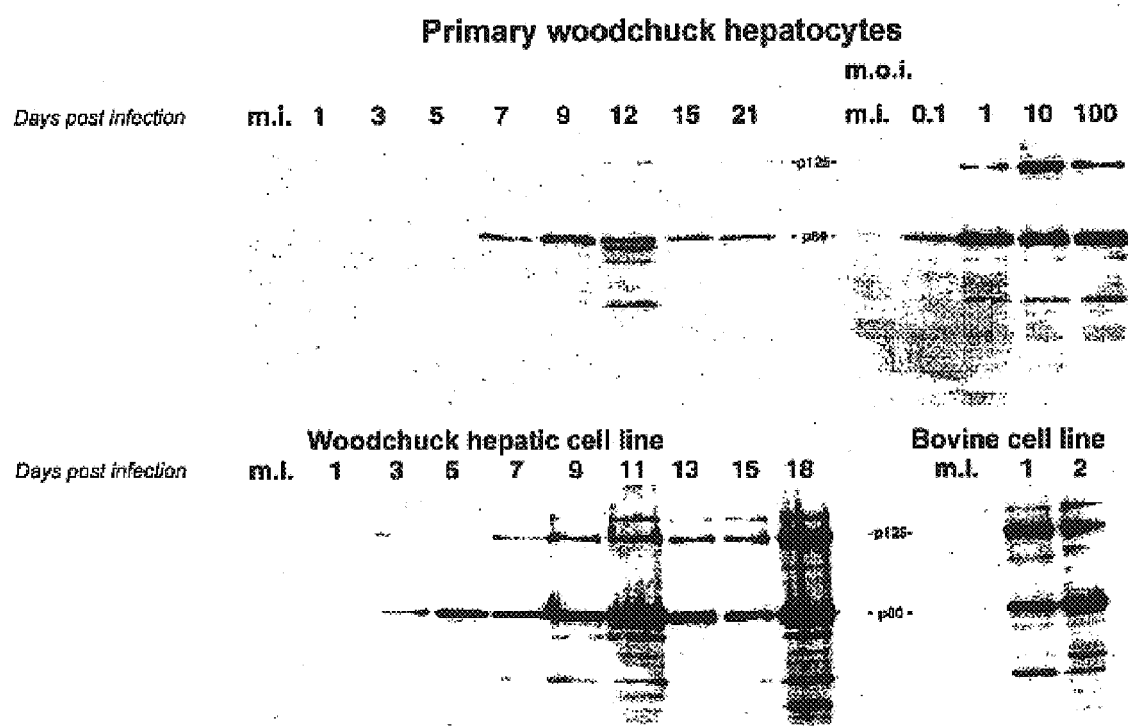
FIG. 9 illustrates BVDV p80 (NS3) expression in woodchuck hepatocytes after inoculation with cpBVDV. Woodchuck primary hepatocytes (A), hepatic WCH-8 (C) and bovine NCL cells (D) were cultured and inoculated with the cytopathogenic NADL isolate of BVDV (cpBVDV). Whole cell homogenates were made at the indicated days post infection (p.i.) and analyzed by immunoblot using a mouse monoclonal antibody specific to BVDV p80. Mock infected cells (m.i.) served as negative controls. The nonstructural protein p80 (NS3) and its precursor molecule p125 (NS2/3) were detected in homogenates beginning day 7 p.i. of primary hepatocytes (A), day 3 p.i. of hepatic WCH-8 cells (C), and day 1 p.i. of bovine NCL cells (D). Woodchuck primary hepatocytes were inoculated with an increasing multipilicity of infection (m.o.i.) of cpBVDV and p80 expression analyzed day 11 p.i. (C).

One phenomenon associated with cytopathogenic isolates of BVDV is the expression of the non-structural viral protein p80 (NS3; serine protease). A similar association between CPE and p80 expression in BVDV-infected woodchuck cells was examined by immunoblot (FIG. 9). The expression of p80 was not detected by immunoblot until 1 week post-infection in cell homogenates of cpBVDV-infected woodchuck primary hepatocytes (FIG. 9A). The expression of p80 was detected as early as 1 day post-infection and increased over time (FIG. 9C), paralleling an increase in viral titers and onset of CPE in WCH-8 cells. Both the precursor p125 and processed p80 were detected with MAB 10.2.24 in woodchuck cell homogenates, similar to expression 1 day post-infection in cpBVDV-infected NCL cells (FIG. 9D).

Infection with cpBVDV leads to viral production without apparent CPE in woodchuck primary hepatocyte cultures. Reduced viral load or uptake may account for lower p80 expression, hence lack of discernable CPE in woodchuck primary hepatocytes. Infection with cpBVDV at a m.o.i. of 0.1 to 100 did not result in CPE, although p80 expression was detected by 7 days post-infection, in primary hepatocytes (FIG. 9B). Upon infection with cpBVDV at a m.o.i. of 100, CPE could be detected as early as 3 days post-infection of WCH-8 cells.

Example 10
Expression of p80 (NS3) in Woodchuck Hepatic Cells

The synthesis, transport and function of viral proteins may be affected by the transformed state of the host cell.

Figure 10:
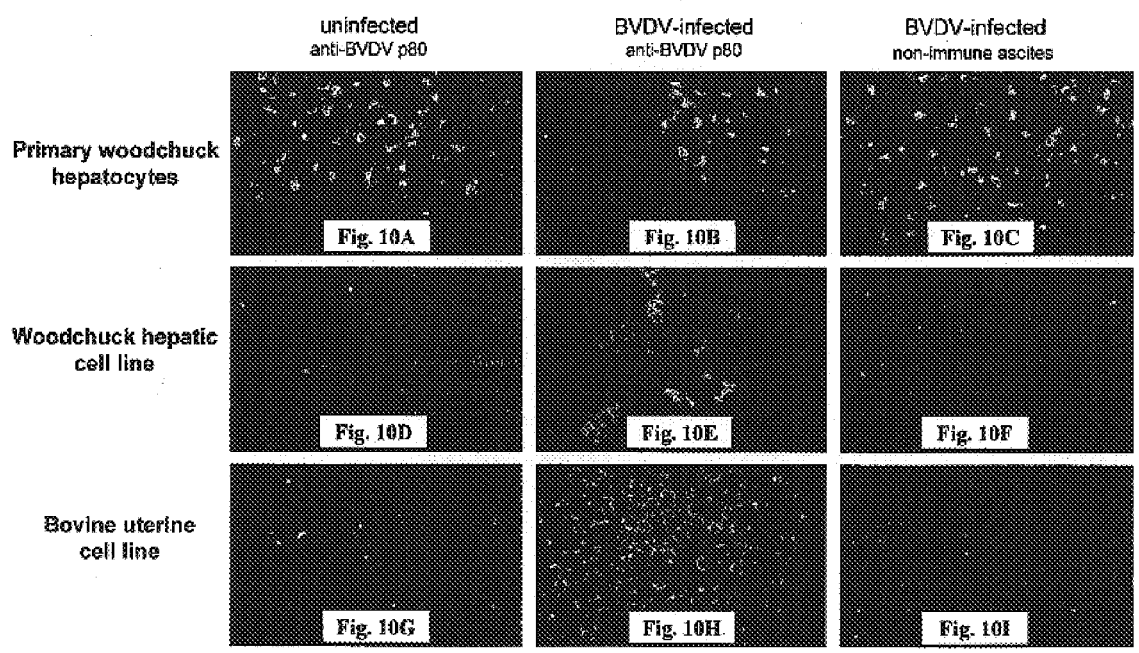
FIG. 10 illustrates the localization of BVDV p80 in woodchuck hepatocytes after inoculation with cpBVDV. Woodchuck primary hepatocytes (A and B), hepatic WCH-8 (C and D) and bovine NCL (E and F) cells were cultured and either mock infected (A, C, and E) or inoculated with the cytopathogenic NADL isolate of BVDV (B, D, and F). Cells were fixed in acetone and stained using a mouse monoclonal antibody specific to cpBVDV p80 (NS3) and FITC-conjugated goat anti-mouse Ig to allow localization of p80 in the cytoplasm of cpBVDV-infected cells by fluorescence microscopy (B, D, and F). BVDV-infected cells stained with non-immune mouse ascites did not exhibit fluorescence (data not shown).

Localization of p80 expression was examined by immunofluorescence in cpBVDV-infected woodchuck hepatocytes and WCH-8 cells (FIG. 10). A characteristic cytoplasmic staining pattern was observed for p80 expression in woodchuck primary hepatocytes and in WCH-8 cells (FIGS. 10B&E). These results were similar to observations with cpBVDV-infected NCL cells (FIG. 10H). Uninfected cells did not exhibit p80 expression when stained with MAB 10.2.24 (FIGS. 10A, D, and G) and cpBVDV-infected cells did not exhibit fluorescence when stained with non-specific, normal mouse ascites as controls (FIGS. 10C, F, and I).

Example 11
BVDV Protein Expression in Woodchuck Hepatic Cells

Figure 11:
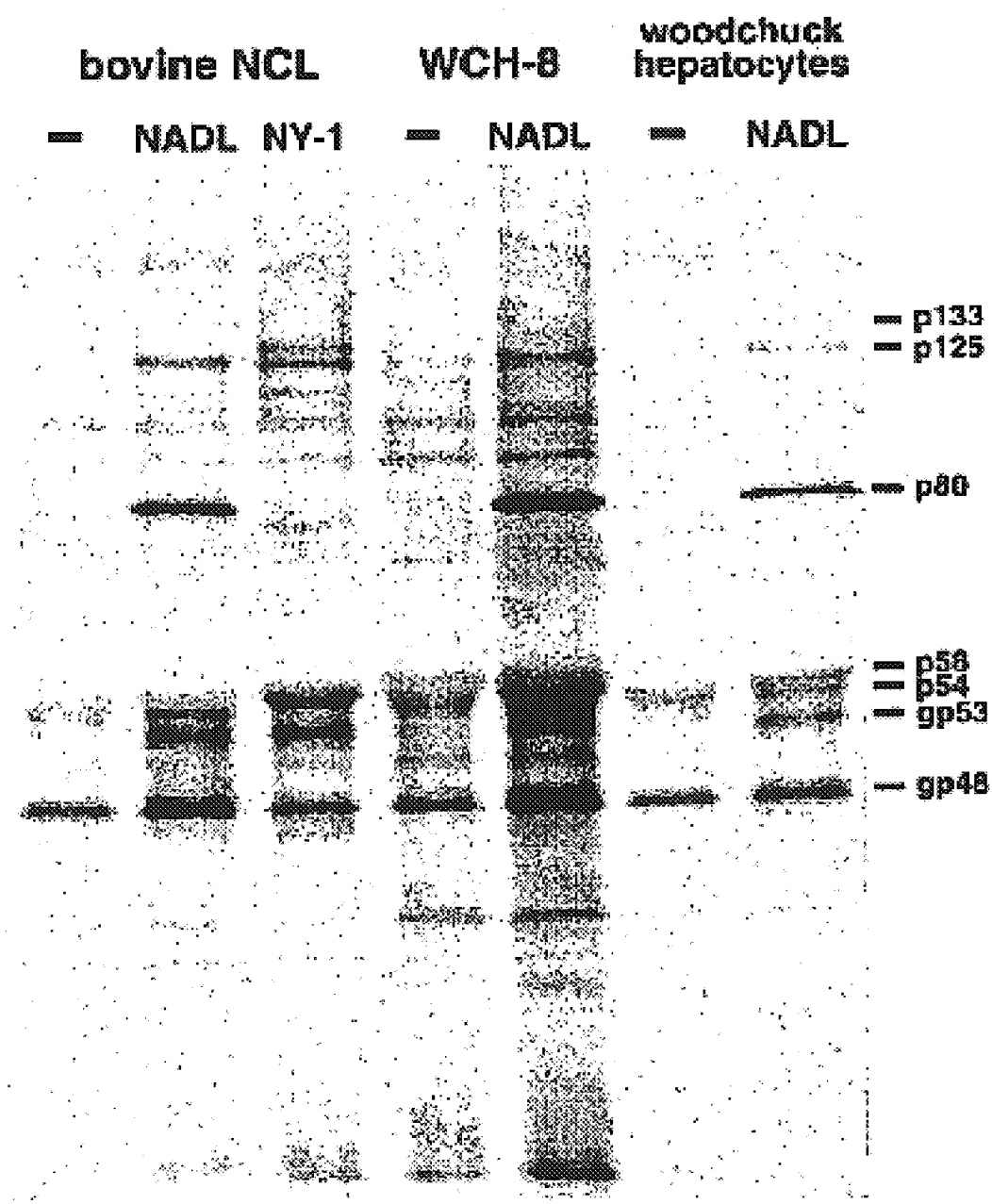
FIG. 11 illustrates the de novo synthesis of BVDV structural and nonstructural proteins in woodchuck hepatocytes after inoculation with cpBVDV. Woodchuck primary hepatocytes, hepatic WCH-8 and bovine NCL cells were cultured and inoculated with BVDV (cytopathogenic NADL; noncytopathogenic NY-1). Extracts of [$^{35}$S]met-cys labeled cultures were immunoprecipitated using hyperimmune bovine serum, separated by SDS-PAGE, and BVDV specific proteins visualized by fluorography on x-ray film. Mock infected cells (m.i.) served as negative (−) controls. The migration of BVDV proteins are indicated to the right of the panel. Nonstructural protein p80 and p53 are not expressed in noncytopathogenic (NY-1) BVDV-infected cells.

Syntheses of both the structural and nonstructural BVDV proteins are required for viral replication in permissive cells. To fully assess the permissive state of woodchuck hepatocytes to BVDV infection, viral protein synthesis was analyzed by immunoprecipitation. Hyperimmune cow serum was used to precipitate BVDV specific antigens from extracts of woodchuck primary hepatocytes, WCH-8 and bovine NCL cells (FIG. 11). BVDV-infected NCL cells were used as a reference and the nonstructural proteins; p133 (NS5A/B), p125 (NS2/3), p80 (NS3), p58 (NS5A), and p54 (NS2), were identified along with the structural proteins; gp48 (E0) and gp53 (E2). The viral protein profile was similar among all three cell types.

Example 12
Antiviral Effects in Woodchuck Hepatic Cells

Figure 12A:
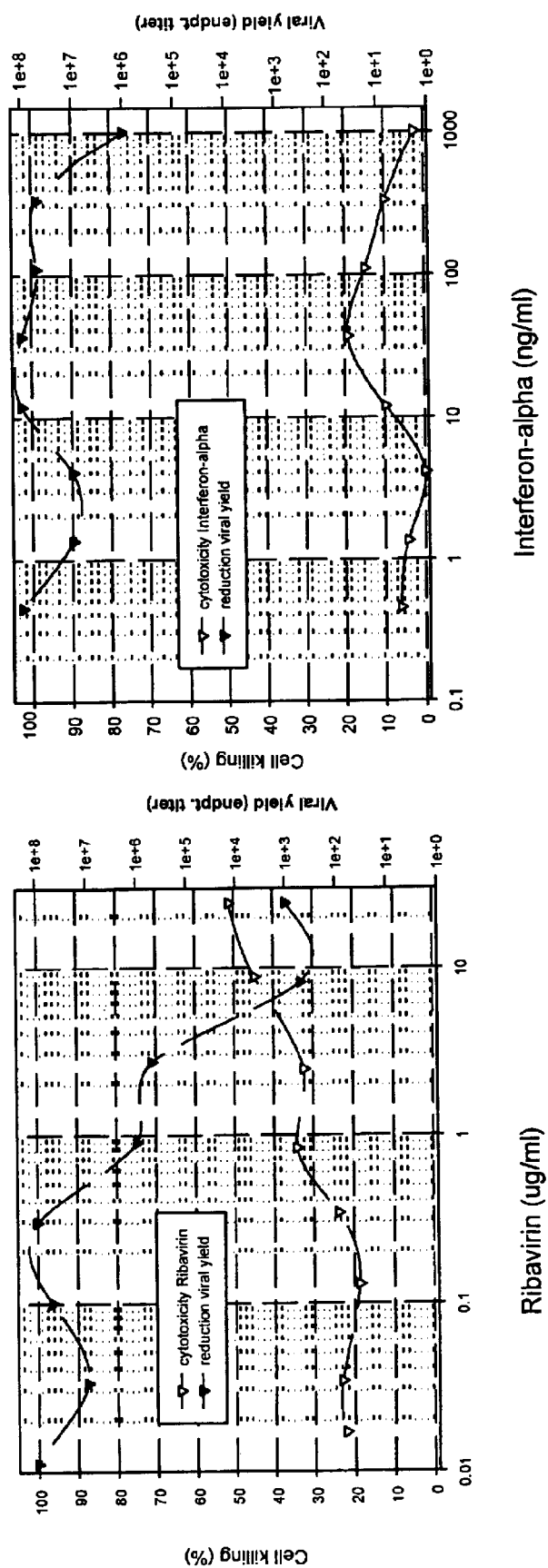
FIG. 12 illustrates the antiviral effects of ribavirin on woodchuck hepatocytes after inoculation with cpBVDV. Woodchuck primary hepatocytes (A), hepatic WCH-8 (B), and bovine NCL cells (C) were cultured in a 96 well format, after infection and antiviral treatment the reduction in cell killing (-●-) and viral yield (-▼-) from cpBVDV-infected cells, and the cytotoxicity (-▽-) of the drug on uninfected cells were measured. Linear regressions were used to calculate the effective drug concentrations described in the text. Due to lack of CPE in primary hepatocytes the reduction in viral-induced cell killing was not calculated (A).
Figure 12B:
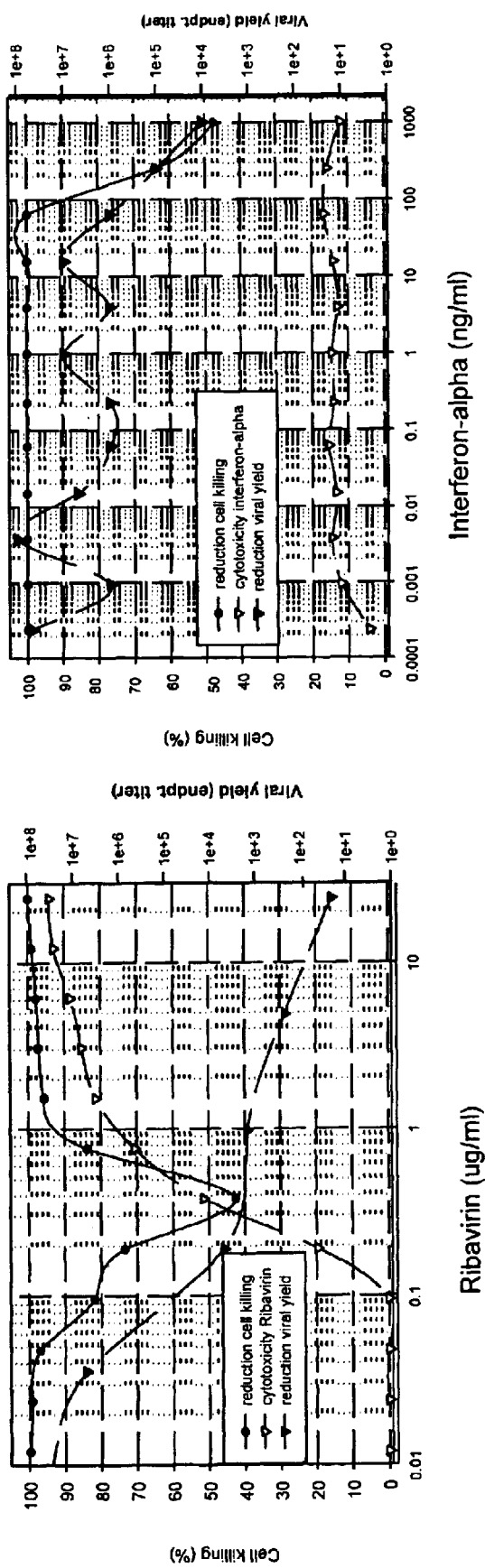

Ribavirin is a synthetic, non-interferon-inducing, broad-spectrum antiviral nucleoside used for the therapeutic treatment for chronic HCV infections in humans. Ribavirin was tested on cpBVDV-infected woodchuck primary hepatocytes and WCH-8 cells, and bovine NCL cells (FIG. 12). The reduction in viral yield ($_rEC_{90}$), reduction of viral induced cell killing ($_{ck}EC_{50}$) and the cytotoxicity ($CC_{50}$) of the antiviral on uninfected cells were determined. The $CC_{50}$ was 44.8 $\mu$M, 2.9 $\mu$M, and 4.3 $\mu$M; and the $_rEC_{90}$ was 3 $\mu$M, 1.1 $\mu$M, and 3.1 $\mu$M for primary hepatocytes, WCH-8, and NCL cells respectively. Due to the lack of viral-induced CPE in woodchuck primary hepatocytes the antiviral effect against cell killing was not calculated, the $_{ck}EC_{50}$ was 1.5 $\mu$M and 5.2 $\mu$M for WCH-8 and NCL cells respectively. A selectivity index ($CC_{50}/_rEC_{90}$) for Ribavirin was 14.9, 2.7, and 1.7 in primary hepatocytes, WCH-8, and NCL cells respectively.

Many modifications and other embodiments of the invention will be apparent to one skilled in the art to which this invention pertains having the benefit of the teachings presented in the foregoing descriptions and the associated drawings. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

What is claimed is:

1. An isolated woodchuck cell infected with bovine viral diarrhea virus.

2. The cell of claim 1, wherein the virus is a noncytopathogenic virus.

3. The cell of claim 1, wherein the cells are in a solution.

4. The cell of claim 3, wherein the solution is a growth medium containing a nutrient supplement selected from the group consisting of fetal bovine serum, horse serum, and cytokines.

5. A method for identifying a compound with potential for treatment of Flaviviridae infection comprising:
   a) administering a test compound to a woodchuck infected with bovine viral diarrhea virus; and
   b) determining whether the test compound inhibits bovine diarrhea virus in the woodchuck;
   wherein inhibition of bovine diarrhea virus identifies a compound with potential for treatment of Flaviviridae infection.

6. A method for selecting a compound with potential for the treatment of a Flaviviridae infection comprising:
   a) administering a test compound to a first woodchuck infected with bovine viral diarrhea virus;
   b) administering a control compound to a second woodchuck infected with bovine viral diarrhea virus; and
   c) selecting the test compound that inhibits bovine viral diarrhea virus in the first woodchuck more than the control inhibits the virus in the second woodchuck.

7. A method for selecting a compound with potential for the treatment of a Flaviviridae infection comprising:
   a) administering a test compound to a first woodchuck infected with bovine viral diarrhea virus;
   b) infecting a second woodchuck with bovine viral diarrhea virus; and
   c) selecting the test compound that decreases the load of bovine viral diarrhea virus in the first woodchuck over the viral load in the second woodchuck.

8. The method of claim 5, wherein the Flaviviridae is hepatitis C.

9. The method of claim 6, wherein the Flaviviridae is hepatitis C.

10. The method of claim 7, wherein the Flaviviridae is hepatitis C.

11. The method of claim 5, 6 or 7, wherein the inhibition of bovine viral diarrhea virus is determined by monitoring the activity of liver enzymes.

12. The method of claim 5, 6 or 7, wherein the inhibition of bovine viral diarrhea virus is determined by assessing the level of bovine viral diarrhea virus antigens present in serum.

13. A method for identifying a compound with potential for treatment of Flaviviridae infection comprising:
   a) administering a test compound to a woodchuck cell infected with bovine viral diarrhea virus; and
   b) determining whether the test compound inhibits bovine diarrhea virus in the woodchuck cell;
   wherein inhibition of bovine diarrhea virus identifies a compound with potential for treatment of Flaviviridae infection.

14. A method for identifying a compound with potential for treatment of Flaviviridae infection comprising:
   a) administering a test compound to a first woodchuck cell infected with bovine viral diarrhea virus;
   b) administering a control compound to a second woodchuck cell infected with bovine viral diarrhea virus; and
   c) determining whether the test compound inhibits bovine diarrhea virus in the first woodchuck cell more than the control compound inhibits bovine viral diarrhea virus in the second woodchuck cell;
   wherein greater inhibition of bovine viral diarrhea virus in the first cell identifies a compound with potential for treatment of Flaviviridae infection.

15. The method of claim 13 or 14 wherein the inhibition of bovine viral diarrhea virus is determined by assessing the level of bovine viral diarrhea virus proteins secreted in culture, detecting viral RNA expression, or detecting viral proteins expressed on cell membranes.

16. The method of claim 13, wherein the infection is a hepatitis C viral infection.

17. The method of claim 14, wherein the infection is a hepatitis C viral infection.

* * * * *